(12) United States Patent
Garcia Santa et al.

(10) Patent No.: US 10,943,679 B2
(45) Date of Patent: Mar. 9, 2021

(54) COMPUTER APPARATUS AND METHOD TO IDENTIFY HEALTHCARE RESOURCES USED BY A PATIENT OF A MEDICAL INSTITUTION

(71) Applicant: Fujitsu Limited, Kawasaki (JP)

(72) Inventors: Nuria Garcia Santa, Madrid (ES); Boris Villazón-Terrazas, Madrid (ES); Victor De La Torre, Madrid (ES)

(73) Assignee: FUJITSU LIMITED, Kawasaki (JP)

( * ) Notice: Subject to any disclaimer, the term of this patent is extended or adjusted under 35 U.S.C. 154(b) by 714 days.

(21) Appl. No.: 15/670,529

(22) Filed: Aug. 7, 2017

(65) Prior Publication Data
US 2018/0101648 A1    Apr. 12, 2018

(30) Foreign Application Priority Data
Oct. 6, 2016    (DE) .................. 10 2016 219 434

(51) Int. Cl.
| | | |
|---|---|---|
| *G16H 10/60* | (2018.01) | |
| *G16H 40/20* | (2018.01) | |
| *G06Q 10/06* | (2012.01) | |
| *G16H 50/70* | (2018.01) | |
| *G16H 50/30* | (2018.01) | |

(Continued)

(52) U.S. Cl.
CPC ......... *G16H 10/60* (2018.01); *G06Q 10/0631* (2013.01); *G16H 20/10* (2018.01); *G16H 20/70* (2018.01); *G16H 40/20* (2018.01); *G16H 50/20* (2018.01); *G16H 50/30* (2018.01); *G16H 50/50* (2018.01); *G16H 50/70* (2018.01); *G06Q 50/22* (2013.01)

(58) Field of Classification Search
None
See application file for complete search history.

(56) References Cited

U.S. PATENT DOCUMENTS

| | | | |
|---|---|---|---|
| 8,015,136 B1 * | 9/2011 | Baker ................... | G16H 50/30 706/45 |
| 8,073,731 B1 * | 12/2011 | Rajasenan .......... | G06Q 10/0637 705/7.42 |

(Continued)

OTHER PUBLICATIONS

Process Mining, Sep. 2016, Wikipedia (Year: 2016).*

(Continued)

*Primary Examiner* — Janice A Mooneyham
*Assistant Examiner* — Karen A Hranek
(74) *Attorney, Agent, or Firm* — Staas & Halsey LLP

(57) ABSTRACT

A computer apparatus to identify healthcare resources used by a medical institution, comprising: a memory storing instructions for execution by a processor, the processor configured by the instructions to provide: a knowledge graph builder; and a knowledge graph customizer; wherein: the knowledge graph builder is arranged to input open data and clinician information, to generate a set of medical services terms and a set of medical resources terms from the open data and clinician information, and to associate the medical resources with the medical services to build a knowledge graph; and the knowledge graph customizer is arranged to match the knowledge graph with records of the medical institution to provide a customized subgraph of the knowledge graph which is specific to the medical institution.

10 Claims, 20 Drawing Sheets

(51) Int. Cl.
*G16H 50/50* (2018.01)
*G16H 20/70* (2018.01)
*G16H 50/20* (2018.01)
*G16H 20/10* (2018.01)
*G06Q 50/22* (2018.01)

(56) References Cited

U.S. PATENT DOCUMENTS

| | | | |
|---|---|---|---|
| 8,407,081 B1 | 3/2013 | Rajasenan | |
| 2001/0016821 A1* | 8/2001 | DeBusk | G06Q 10/08 |
| | | | 705/2 |
| 2003/0060688 A1* | 3/2003 | Ciarniello | G06Q 40/08 |
| | | | 600/300 |
| 2006/0074720 A1 | 4/2006 | Brutting et al. | |
| 2007/0005621 A1* | 1/2007 | Lesh | G16H 15/00 |
| 2012/0173253 A1 | 7/2012 | Reynolds et al. | |
| 2013/0096947 A1* | 4/2013 | Shah | G06Q 50/24 |
| | | | 705/3 |
| 2014/0236625 A1* | 8/2014 | Hartman | G06Q 50/01 |
| | | | 705/3 |
| 2014/0249848 A1* | 9/2014 | Averill | G16H 10/60 |
| | | | 705/3 |
| 2015/0095303 A1* | 4/2015 | Sonmez | G06N 5/003 |
| | | | 707/707 |
| 2016/0283880 A1 | 9/2016 | Jin | |
| 2017/0235888 A1* | 8/2017 | Rahman | G06F 40/295 |
| | | | 705/3 |
| 2018/0039696 A1* | 2/2018 | Zhai | G06F 16/35 |

OTHER PUBLICATIONS

Wang et al., Creating hospital-specific customized clinical pathways by applying semantic reasoning to clinical data, Aug. 8, 2014, Journal of Biomedical Informatics 52, 354-363 (Year: 2014).*
German search report dated Jul. 17, 2017 in corresponding German Patent Application No. 102016219434.8.
European search report dated Jul. 21, 2017 in corresponding European Patent Application No. 17166978.1.
Jianying Hu et al., "A Healthcare Utilization Analysis Framework for Hot Spotting and Contextual Anomaly Detection" American Medical Informatics Association Annual Symposium Proceedings pp. 360-369.

* cited by examiner

Figure 4

COMPUTER APPARATUS AND METHOD TO IDENTIFY HEALTHCARE RESOURCES USED BY A PATIENT OF A MEDICAL INSTITUTION

CROSS-REFERENCE TO RELATED APPLICATIONS

This application claims the benefit of German Application No. 102016219434.8, filed Oct. 6, 2016, in the German Intellectual Property Office, the disclosure of which is incorporated herein by reference.

The embodiments relates to medical resource utilization by an individual or a living subject, usually referred to as a patient. The patient may be a human or potentially an animal, such as a specimen of a rare breed or even a pet. The patient is of a medical institution, such as a hospital, or doctor's, dentist's or veterinarian's practice. The term medical institution can also cover a medical conglomeration or organization across different locations and hospital/practices.

In many scenarios, the patient may already be suffering from a disorder, but in others the patient is currently healthy, and thus the term medical condition includes conditions such as pregnancy, as well as disorders, illnesses and diseases. The embodiments are thus widely applicable in provision of healthcare and veterinary healthcare.

Resource utilization is the amount of a good or service consumed or the pattern of use of a good or service within a specified time period. Quality care remains the goal in healthcare and outcome-focused plans of care have been shown to contain resource utilization and enhance quality. The success of quality care services depends on good coordination and management of the health care resources utilization in the medical institutions.

Although public and private payers express considerable interest in calculating the value of health care services, it remains a challenge to develop and implement nationally accepted measures. Expenditure prediction models typically incorporate information on clinical conditions based on data from medical records. Some of the approaches to this are (1) the relative risk or risk ratio (RR), (2) the Diagnostic Cost Group (DCG) model, (3) the Medical Episode Grouper (MEG) methodology, (4) and episode treatment group (ETG) methodology.

Several differences among resource use measures could guide a community collaborative's choice of measures. Many resource measures focus on hospitals, including simple measures such as a mean length of stay and more complex multiple-output measures using econometric or mathematical programming techniques.

In addition, patients who have similar clinical characteristics and similar treatment costs may be assigned to an MS-DRG, (Diagnosis-related group— see en.wikipedia.org). The MS-DRG is linked to a fixed payment amount based on the average treatment cost of patients in the group. Patients can be assigned to an MS-DRG based on their diagnosis, surgical procedures, age, and other information. However, there is no relevant work to associate DRGs to medical resources or services.

It is desirable to provide a way of deriving healthcare resource usage which is based on practice and on specific clinical information.

SUMMARY

According to an embodiment of a first aspect, there is provided a computer apparatus to identify healthcare resources used by a patient of a medical institution, comprising: a memory storing instructions for execution by a processor, the processor configured by the instructions to provide: a knowledge graph builder; a knowledge graph customizer and a patient HCRU engine; wherein:

the knowledge graph builder is arranged to input open data and clinician information, to generate a set of medical services terms and a set of medical resources terms from the open data and clinician information, and to associate the medical resources with the medical services to build the knowledge graph;

the knowledge graph customizer is arranged to match the knowledge graph with records of the medical institution to provide a customized subgraph of the knowledge graph which is specific to the medical institution.

The inventors have found a way of identifying healthcare utilization which is tailored to the patient and to the medical institution concerned but which also incorporates a standard framework using open data (for example in the form of one or more publically available healthcare and/or medical services databases) and clinician input, which can act to standardize the results across a population of patients.

All of the aforementioned approaches in the prior art focus directly on calculating the associated costs instead of concentrating first on the resource utilization. One idea behind the embodiments is to derive and focus on health care resource utilization.

In summary, within the healthcare domain, the inventors believe that

- there are no standards for representing health care resource utilization, in the same way as there are standards for diseases, e.g., ICD9; there are only plain lists of health care resources and they are specific to a particular area or region;
- there are no works that associate DRG's to medical resources and services;
- there are no ways to specialize the plain lists of health care resources to the specific needs and reality of a particular hospital institution;
- there is a lack of methods and tools that exploit information about healthcare resource utilization and its association to patient clinical data.

The inventors have come to the conclusion that to achieve good management in health care services it is important to have a standardization which collects and links (a hierarchy of) the different medical services with resources usage. A graph presentation of this standardization is practical for further manipulation and understanding. Moreover, this model should be associated to the specific needs and reality of each medical institution, when possible. This task can leverage semantic technologies and knowledge graph tools to get the benefits of this approach, such as semantic linking and annotating, semantic alignment with external resources, straight publishing and sharing process to establish standards protocols, etc.

Additionally, a patient healthcare resource utilization, HCRU, engine may be arranged to input a patient clinical object, PCO, which represents the patient in the form of a graph, and to use the customized subgraph to associate and annotate the PCO with relevant healthcare resource utilization information. This way of identifying healthcare utilization is tailored to the patient as well as to the medical institution concerned. Thus it allows identification of the resources used by a specific patient of a medical institution.

The knowledge graph builder may function in any appropriate way. It may be configured to collect seeds (for example in the form of suggested terms) for an initial set of medical services terms and seeds for an initial set of medical resources terms from the clinician information. It may then reconcile the collected initial sets of terms from the clinician with the open data to provide an enhanced set of terms proposed by the clinicians and annotated using the open data. This allows a more generic and standardized set of terms which is widely applicable and thus of better quality for the following process.

The knowledge graph builder may be to create two models (separately), one representing healthcare resources and the other representing healthcare services.

The knowledge graph builder can then create relations between the two models, using relation mining in the open data, scoring the relations according to the number of occurrences of the relations in the open data. The occurrence scoring can use any suitable methodology, usually based on co-occurrence of the terms in the same dataset or within a predefined distance in the same dataset for example.

The knowledge graph customizer functions to fit the medical institution and knowledge graph data together. It may identify services of the medical institution that are represented in the knowledge graph. It may filter out services in the knowledge graph that are not provided in the medical institution. Importantly, it may identify what resources are used from medical institution data and remove resources from the knowledge graph that are not available in the medical institution.

The knowledge graph customizer may use process mining to discover how resources are used in the medical institution (in terms of what services use what resources) and to adapt the knowledge graph to the particular way that resources are used in the medical institution.

The knowledge graph customizer may be configured to input an electronic medical institution log and internal regulations of the medical institution. It can then extract process knowledge from the electronic medical institution log (using known process mining techniques) and project the extracted process knowledge onto the internal regulations of the medical institution to check if the extracted process knowledge conforms to the internal regulations of the medical institution.

The patient HCRU engine can use any suitable methodology to add the resource data to the PCO. It may use clinical data present in the PCO and add links to new vertices representing healthcare resources, using the customized subgraph of the knowledge graph as a template (for instance by using the links in the knowledge graph between services and resources to link the same or similar services in the PCO to new resources, which are taken from the corresponding position in the knowledge graph).

The PCO may be provided as a graph centered on a patient ID vertex, with edges linking the patient ID vertex to vertices representing clinical data, and the patient HCRU engine matches the vertices representing clinical data to vertices of the knowledge graph.

The PCO may be limited (by the user or automatically) to one or more of: a condition, an episode of a condition, a timeframe, and a diagnosis.

The embodiments are not limited in application to a single patient, but can be used to assess healthcare resource utilization of a population of patients. Hence the computer apparatus may be to identify healthcare resources used by a population of patients of a medical institution, by inputting a patient clinical object, PCO, for each patient, and by using the customized subgraph to associate and annotate each PCO with relevant healthcare resource utilization information. Any of these preferred features relating to the PCO and patient HCRU engine can be combined with any of the other preferred features mentioned above.

According to an embodiment of a second aspect, there is provided a computer-implemented method to identify healthcare resources used by a medical institution, comprising:

inputting open data and clinician information, generating a set of medical services terms and a set of medical resources terms from the open data and clinician information, and associating the medical resources with the medical services to build a knowledge graph; and matching the knowledge graph with records of the medical institution to provide a customized subgraph of the knowledge graph which is specific to the medical institution.

The method may further include inputting a patient clinical object, PCO, which represents the patient in the form of a graph and using the customized subgraph to associate and annotate the PCO with relevant healthcare resource utilization information.

According to an embodiment of a third aspect, there is provided a computer program which when executed on a computer carries out a method to identify healthcare resources used by a medical institution, comprising:

inputting open data and clinician information, generating a set of medical services terms and a set of medical resources terms from the open data and clinician information, and associating the medical resources with the medical services to build a knowledge graph; and matching the knowledge graph with records of the medical institution to provide a customized subgraph of the knowledge graph which is specific to the medical institution.

An apparatus or computer program according to preferred embodiments can comprise any combination of the method aspects. Methods or computer programs according to further embodiments can be described as computer-implemented in that they require processing and memory capability.

The apparatus according to preferred embodiments is described as configured or arranged to, or simply "to" carry out certain functions. This configuration or arrangement could be by use of hardware or middleware or any other suitable system. In preferred embodiments, the configuration or arrangement is by software.

Thus according to one aspect there is provided a program which, when loaded onto at least one computer configures the computer to become the apparatus according to any of the preceding apparatus definitions or any combination thereof.

According to a further aspect there is provided a program which when loaded onto the at least one computer configures the at least one computer to carry out the method steps according to any of the preceding method definitions or any combination thereof.

In general the computer may comprise the elements listed as being configured or arranged to provide the functions defined. For example this computer may include memory, processing, and a network interface.

The embodiments can be implemented in digital electronic circuitry, or in computer hardware, firmware, software, or in combinations of them. The embodiments can be implemented as a computer program or computer program product, i.e., a computer program tangibly embodied in a non-transitory information carrier, e.g., in a machine-readable storage device, or in a propagated signal, for execution by, or to control the operation of, one or more hardware modules.

A computer program can be in the form of a stand-alone program, a computer program portion or more than one computer program and can be written in any form of programming language, including compiled or interpreted languages, and it can be deployed in any form, including as a stand-alone program or as a module, component, subroutine, or other unit suitable for use in a data processing environment. A computer program can be deployed to be executed on one module or on multiple modules at one site or distributed across multiple sites and interconnected by a communication network.

Method steps can be performed by one or more programmable processors executing a computer program to perform functions of the embodiments by operating on input data and generating output. Apparatus of the embodiments can be implemented as programmed hardware or as special purpose logic circuitry, including e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions coupled to one or more memory devices for storing instructions and data.

The embodiments are described in terms of particular embodiments. Other embodiments are within the scope of the following claims. For example, the steps of the embodiments can be performed in a different order and still achieve desirable results. Multiple test script versions can be edited and invoked as a unit without using object-oriented programming technology; for example, the elements of a script object can be organized in a structured database or a file system, and the operations described as being performed by the script object can be performed by a test control program.

Elements of the embodiments have been described using the terms "knowledge graph builder", "knowledge graph customizer", "patient HCRU engine" etc. The skilled person will appreciate that such functional terms and their equivalents may refer to parts of the system that are spatially separate but combine to serve the function defined. Equally, the same physical parts of the system may provide two or more of the functions defined.

For example, separately defined means may be implemented using the same memory and/or processor as appropriate.

BRIEF DESCRIPTION OF THE DRAWINGS

Preferred features of the embodiments will now be described, purely by way of example, and with references to the accompanying drawings, in which:

FIG. 4 shows an example of the data presented on a web front end of a standard categorization of healthcare resources and other medical information;

DETAILED DESCRIPTION

Figure 1:
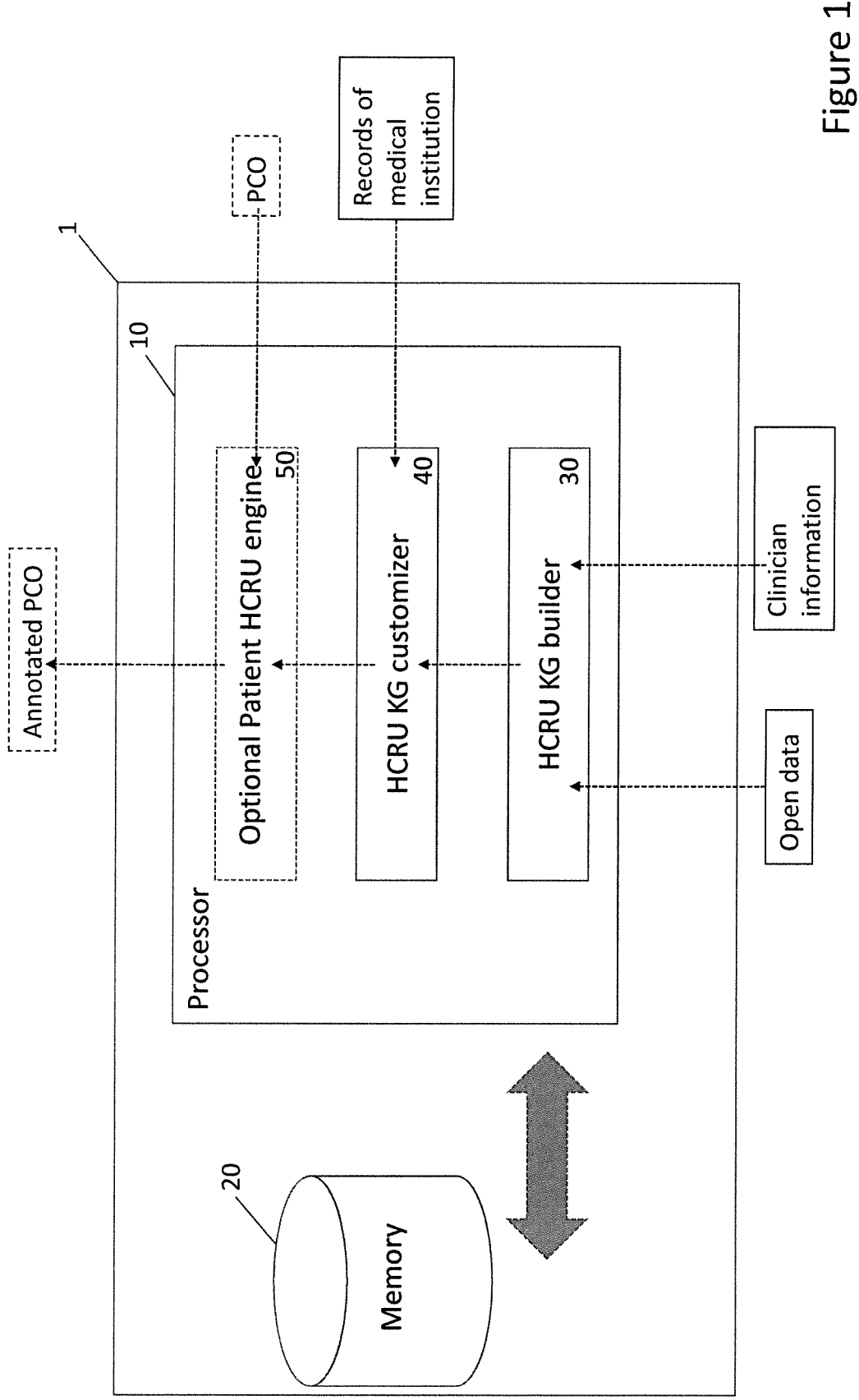
FIG. 1 is a block diagram of main system components in a general.

Reference will now be made in detail to the embodiments, examples of which are illustrated in the accompanying drawings, wherein like reference numerals refer to the like elements throughout. The embodiments are described below to explain the embodiments by referring to the figures.

Embodiments can provide:
  a network of health care resource utilization, represented as a Knowledge Graph, extracted from the literature, public data sources, hospital specific logs and regulations, together with the clinicians' expertise on health care resource utilization;
  optionally, a mechanism that identifies the associated health care resource utilization measure for a particular patient given his/her clinical history information, and enrich the patient clinical history with his/her health care resource utilization information;

Precision medicine is an emerging approach for disease diagnosis, treatment and prevention that takes into account individual variability in genes, physiology, anatomy, environment, and lifestyle. Precision medicine represents a disruption to the current clinical workflows and resource utilization of the healthcare ecosystem. In this context, embodiments create and use a Knowledge Graph (KG) of health resources utilization along with their specific features, and their associated Patient Clinical Object (PCO) i.e. patient's treatments, diagnosis, and drugs.

This solution establishes and implements a valuable precision medicine within academic medical centers and healthcare clients.

BACKGROUND

At the time of writing there is no standard resource for dealing with health resource utilization; there are only ad-hoc resources as plain lists, or matrices for specific areas, for example
  Health Care Cost and Utilization Report (www.healthcostinstitute.org)

U.S. Department of Health and Human Services (www.www.cdc.gov).

Moreover, there are some organizations that are developing resource use measures, for specific regions, and countries Agency for Healthcare Research and Quality (www.ahrq.gov/), which includes a chapter of efficiency.

Centers for Medicare & Medicaid Services (www.cms.gov/)

National Committee for Quality Assurance (www.ncqa.org)

Quality Alliance Steering Committee (www.healthqualityalliance.org/)

European Health for All database, World Health Organization, European Region (www.euro.who.int).

As medical societies, provider organizations, and others look for ways to drive appropriate use of medical resources, hospitals and health systems can play an important role in supporting and guiding these efforts within their organizations. One of the first steps is to identify what is the health care resource utilization among hospital patients. However, efforts to identify this have so far been quite limited.

After having analyzed the related works on health care resources utilization knowledge base the inventors can state that there are no standards for representing health care resource utilization, in the same way as there are standards for diseases, e.g., ICD9; there are only plain lists of health care resources and they are specific to a particular area, region or country;

there is a lack of methods and tools to extract, curate, reconcile and integrate data about health care resource utilization, and its specific features, from medical institutions, databases, repositories and ontologies;

there are no ways to specialize the plain lists of health care resources to specific needs and reality of a particular hospital institution;

General Description

Invention embodiments create a Knowledge Graph of health care resource utilization along with specific features and their relations among health care resources and services. Moreover, some embodiments enrich the Patient Clinical Object, PCO, by including the associated health care resource utilization for a particular patient.

The system in preferred embodiments can include a main core module:

A module for the creation and maintenance of Health Care Resource Utilization Knowledge Graph (HCRU KG), based on information extracted from the literature and public data sources together with the clinicians' expertise on that matter; and a possible further module A module that associates and annotates the patient clinical history with the HCRU, creating in this way a Patient HCRU sub-graph.

and an optional module:

A module that estimates the impact of a potential new diagnosis in the patient, in terms of health care resource utilization.

FIG. 1 shows a general embodiment of a computer apparatus to identify healthcare resources used by a patient of a medical institution. The apparatus 100 includes memory 20 and a processor 10, with the processor implementing various modules, using the memory for storage. It does not include the optional module which estimates the impact of a potential new diagnosis.

The processor 10 is arranged to provide: a knowledge graph builder in the form of a healthcare resource utilization, HCRU, knowledge graph, KG, builder 30; a knowledge graph (HCRU KG) customizer 40. It may also provide a patient HCRU engine 50 in some preferred embodiments, and this further module is hence shown in dashed lines.

The HCRU KG builder is arranged to receive open data about medical resources and healthcare service and clinician information. It generates a set of medical services terms and a set of medical resources terms from the open data and clinician information. It then associates the medical resources with the medical services (for example using relations detected from the open data) to build the HCRU KG.

The HCRU KG customizer is arranged to compare the HCRU KG with records of the medical institution to provide a customized subgraph of the HCRU KG, which is thus based on the resources from the overall HCRU KG which are available in the medical institution. This allows resources of the medical institution to be linked to the medical services using a generally applicable model.

The patient HCRU engine receives a patient clinical object, PCO, which represents the patient in the form of a graph centred on a patient ID vertex, with edges linking the patient ID vertex to vertices representing clinical data. It uses the customized subgraph to associate the PCO with relevant healthcare resource utilization information and to annotate the PCO with this information. This identifies the healthcare resources used by the patient.

The PCO (or PCOs if more than one is being used) may be limited to a certain time frame, for example a month or a week, or to an episode of a condition or to a certain diagnosis or condition. In this way, specific information can be captured which may be useful for directed analysis.

Figure 2:
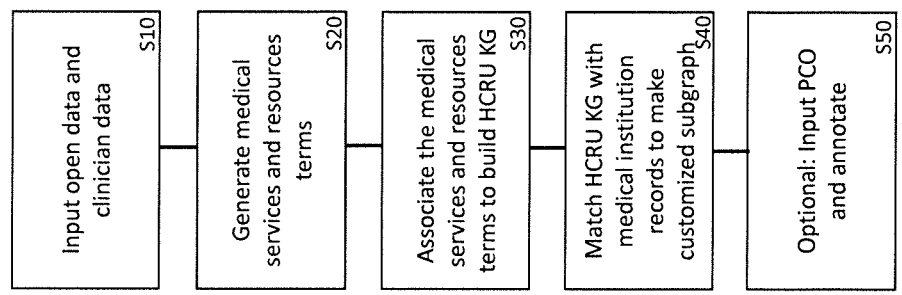
FIG. 2 is a flow chart of a method in a general embodiment.

FIG. 2 is a flow chart of a general embodiment providing a computer-implemented method to identify healthcare resources used by a medical institution. The method includes the following processes:

S10, input open data and clinician information; S20, generate a set of medical services terms and a set of medical resources terms from the open data and clinician information; S30 associate the medical resources with the medical services to build a healthcare resource utilization, HCRU, knowledge graph, KG; and S40, match the HCRU KG with records of the medical institution to provide a customized subgraph of the HCRU KG which is specific to the medical institution. The method can also include S50, inputting a patient clinical object, PCO, which represents the patient in the form of a graph and use the customized subgraph to associate and annotate the PCO with relevant healthcare resource utilization information.

Detailed Description of a Particular Embodiment

Figure 3:
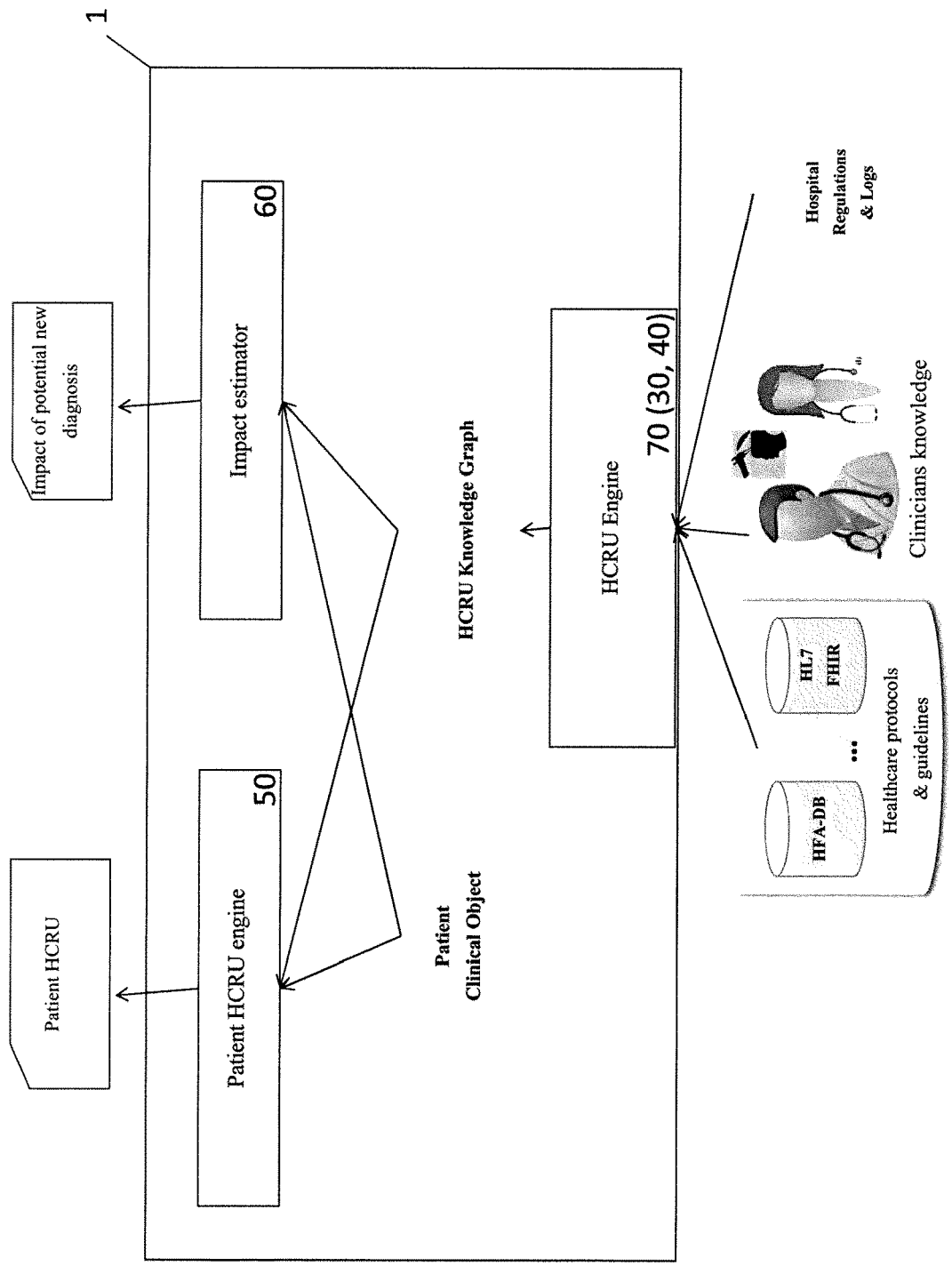
FIG. 3 is a diagram of a specific embodiment.

As shown in FIG. 3, one embodiment of the system includes a Health Care Resource Utilization (HCRU) Knowledge Graph (KG) Engine module 70, which uses open data such as information obtained from the relevant online literature, and available standards. This HCRU KG engine encompasses the healthcare resource utilization, HCRU, knowledge graph, KG, builder 30 and the HCRU KG customizer 40. The patient HCRU graph engine module 50 associates/annotates the existing patient clinical history with the HCRU Knowledge Graph. The optional impact estimator module 60 estimates the impact of a potential new diagnosis on the patient, in terms of health care resource utilization graph.

It is worth mentioning that some embodiments rely on the "Patient Clinical Object" that is defined as a semantically rich aggregation of clinical entities that encapsulates information about a given patient. This PCO contains information about the patient and its clinical data, including diagnoses, drugs, symptoms and services used.

PCO

The PCO may be provided by a PCO builder (not shown). This PCO builder module can be part of the system, or provided by a separate system. It takes as input the following information:

Expert knowledge provided by doctor/clinicians in the form of rules coded in a computer language. The clinicians input the rules as text plain files. Basically, the file consists of several rows, and each row contains 2 diagnoses and the relation between them. For example:

Diagnosis1,relationA,Diagnosis2
Diagnosis3,relationB,Diagnosis4

Examples of rules are incompatible diagnoses, and prevalence of diagnosis
290.0, prevailing over, 290.4
300.0, incompatible with, 309

Where 290.0 corresponds to Senile dementia, uncomplicated, and 290.4 corresponds to Vascular dementia. Also, 300.0 corresponds to Anxiety states, and 309 corresponds to Adjustment reaction.

Previous diagnoses provided by other clinicians as they are recorded in the patient clinical history. These diagnoses will be based on existing international standards such as ICD9 and ICD10 (the ninth and tenth revisions of the International Classification of Diseases).

Data related to the patient's visits to the hospital and the associated points of care, including the frequency, timeframe, and any resources the patient has used, if this resource information has been included on an ad hoc basis in the patient's notes.

Biomedical research literature, extracted from literature repositories such as PUBMED, related to diagnoses, diseases, treatments, etc (PUBMED is a service of the US National Library of Medicine (NLM) and provides free access to the NLM database of nursing, veterinary, healthcare, medical and scientific articles).

Prescription and dispensing of drugs, and their adverse drug reaction, based on European and international standards, such as ATC (Anatomical Therapeutic Chemical Classification).

A set of knowledge extracted from available medical standards such as SNOMED CT (a standardised, multilingual vocabulary of terms relating to the care of the individual).

The expert knowledge need not be essential to make the PCO, but can be used to verify and potentially enrich the knowledge in the PCO, for example by adjusting the diagnoses in the PCO using the expert knowledge, to make sure they are in line with current medical thinking. Additionally or alternatively, any diagnoses in the PCO which are in contradiction with the expert knowledge may be highlighted to the user for manual input and in this way the expert knowledge can act as a cross-check for the quality of the PCOs.

The patient clinical object builder collects, extracts, integrates, curates and cleans the aforementioned data sources and produces the Patient Clinical Object (also known as a patient's egocentric network or ego-net) for each patient, which contains all the related information about the patient, namely age group, gender, a list of hospital visits grouped by unit, e.g., emergency room, outpatient, inpatient, and day hospital, and a list of previous diagnoses grouped by hospital visits and units.

The PCO can be produced from clinical data as a graph centered on the patient vertex, with information about the patient at neighboring vertices linked along edges to the patient by categories, such as any of diagnosis, symptom, treatment, hospital visit and prescription. The clinical data may be provided, for example from hospital records, or health authority records.

The open data (in the last 3 bullet points above) is used for enrichment of the terms. That is, the PCO may be enriched by equating PCO parts with standard vocabulary from the classifications listed above and hence annotating entities in the patient data as necessary with corresponding concepts/information from the open data. This facilitates later use of the PCO in conjunction with other standard data.

HCRU Engine 70

Figure 4:
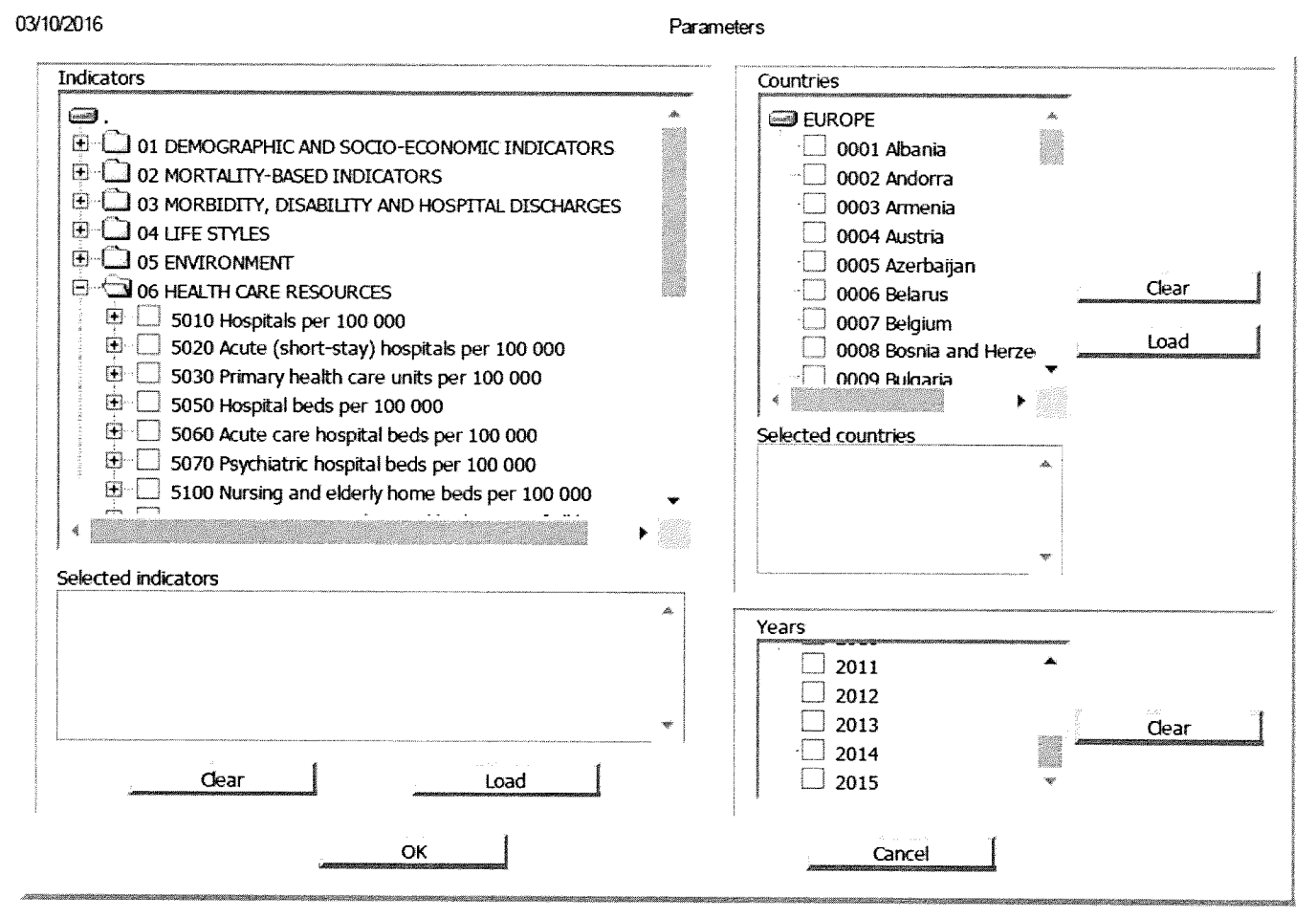

This module captures the evidence based on data derived from literature and public data sources, such HFA-DB, European health for all database, health care resources and health care utilization and expenditure (data.euro.who.int) and HL7-FHIR, Fast Healthcare Interoperability Resources (www.hl7.org). In a nutshell, the aforementioned public data sources organize the healthcare resources and services and provide a web front end for querying the information. The underlying data is stored in a data storage volume. FIG. 4 shows an example of the data presented on the web front end, for HFA-DB.

There are also other plain lists of healthcare services, in some cases only for a particular country or region, e.g., www.wpc-edi.com.

This HCRU Engine module includes two main sub-modules, an HCRU KG builder 30 and an HCRU KG customizer 40, which each in turn consist of several components.

HCRU KG Builder (or HCRU Engine) 30

Figure 5:
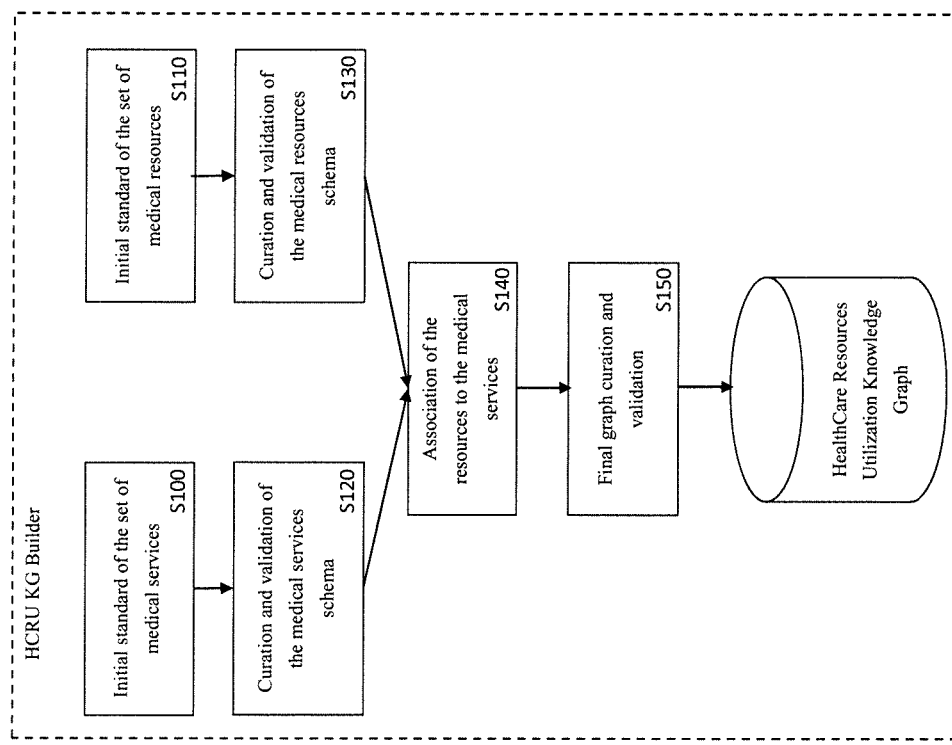
FIG. 5 depicts the main flow of the healthcare resource utilization knowledge graph (HCRU KG) builder sub-module.

FIG. 5 depicts the main flow of this sub-module. This sub-module comprises components which:

collect and generate a set of medical services categories (see S100).

collect and generate a set of healthcare resource utilization related terms (see S110).

reconcile the medical services and healthcare resource utilization related terms to information extracted from the literature and public data sources, such as the database from World Health Organization (www.euro.who.int), generate initial knowledge models from the set of medical services and resource utilization related definitions and links to literature and public data concepts.

validate and curate the initial knowledge graphs, potentially with the help of clinicians' expertise (S120, S130).

perform association between the medial services network with the medical resources utilization parameters (S140).

curate, and refine the resultant entities and relations with the support of the clinicians (S150).

Figure 6:
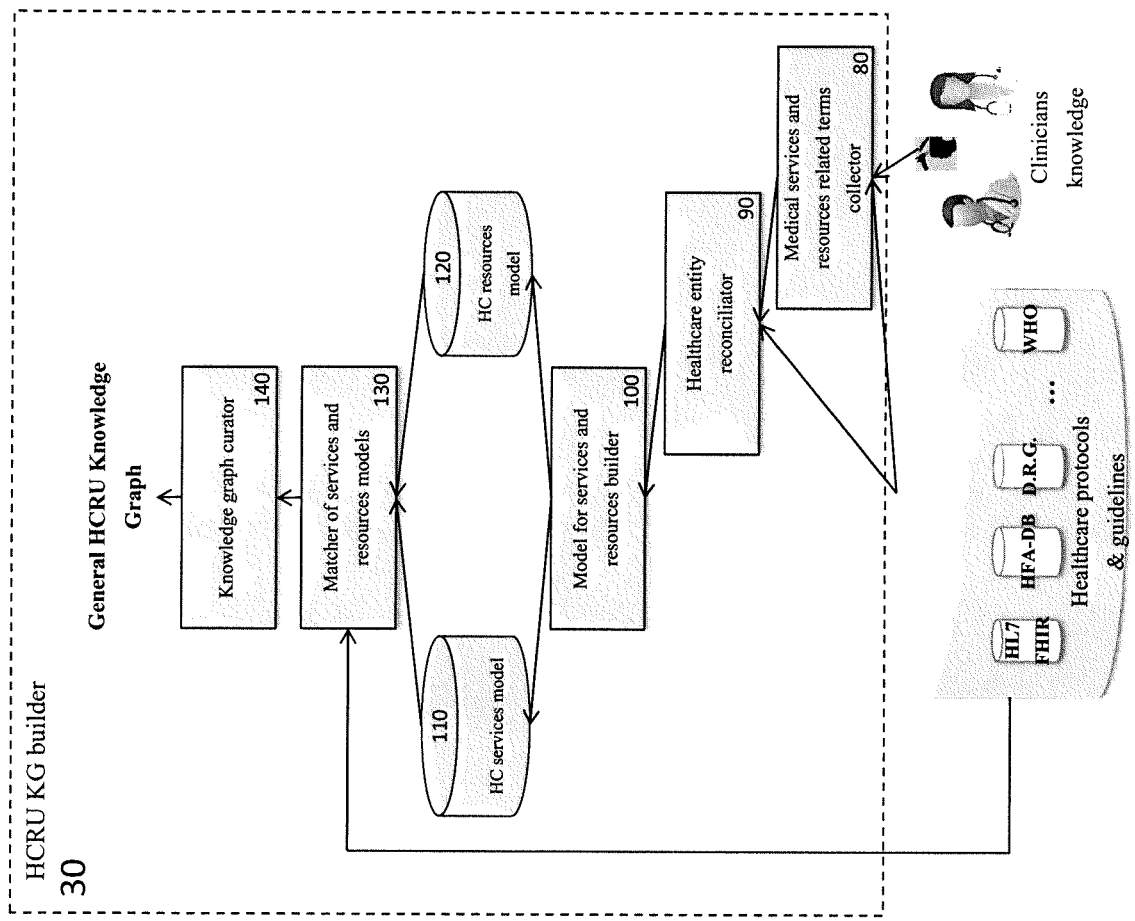
FIG. 6 illustrates the main components of the HCRU KG Builder.

FIG. 6 illustrates the main components of the HCRU KG Builder 30, as explained in more detail below.

Medical Services and Resources Related Terms Collector 80

Figure 7:
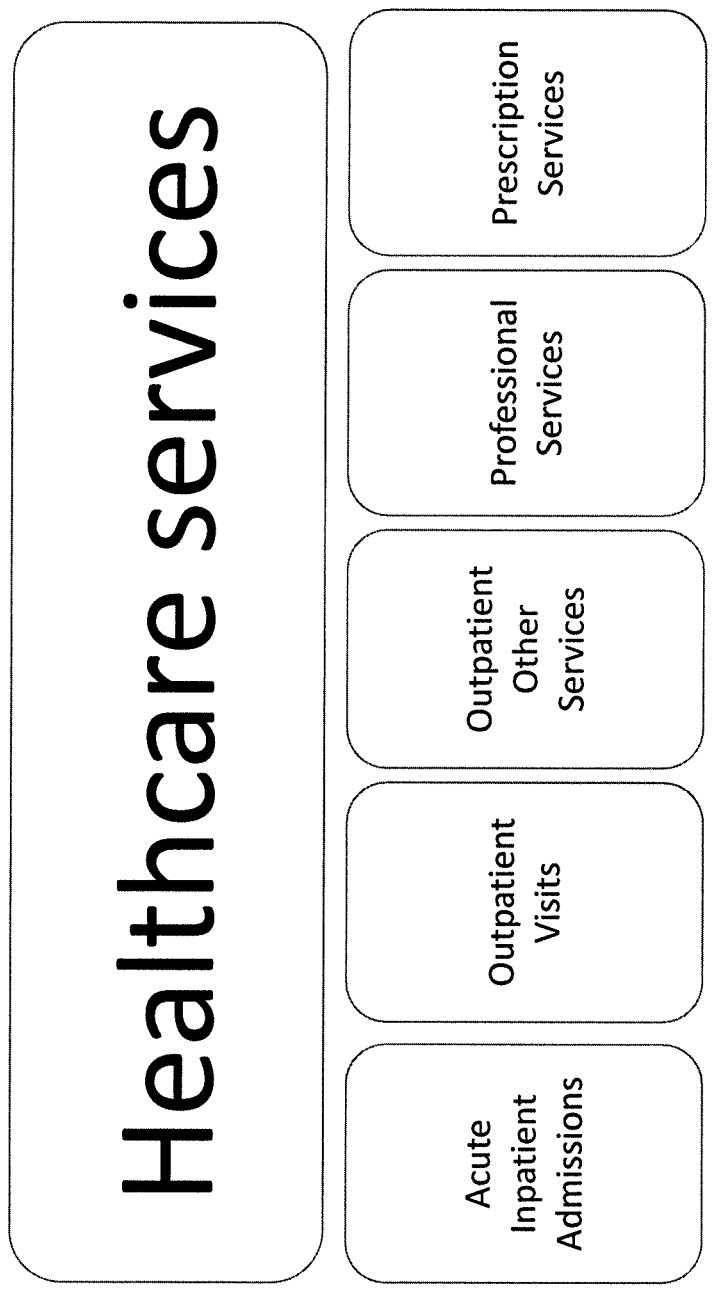
FIG. 7 is a conceptual diagram of top level concepts of an HC service hierarchy model.
Figure 8:
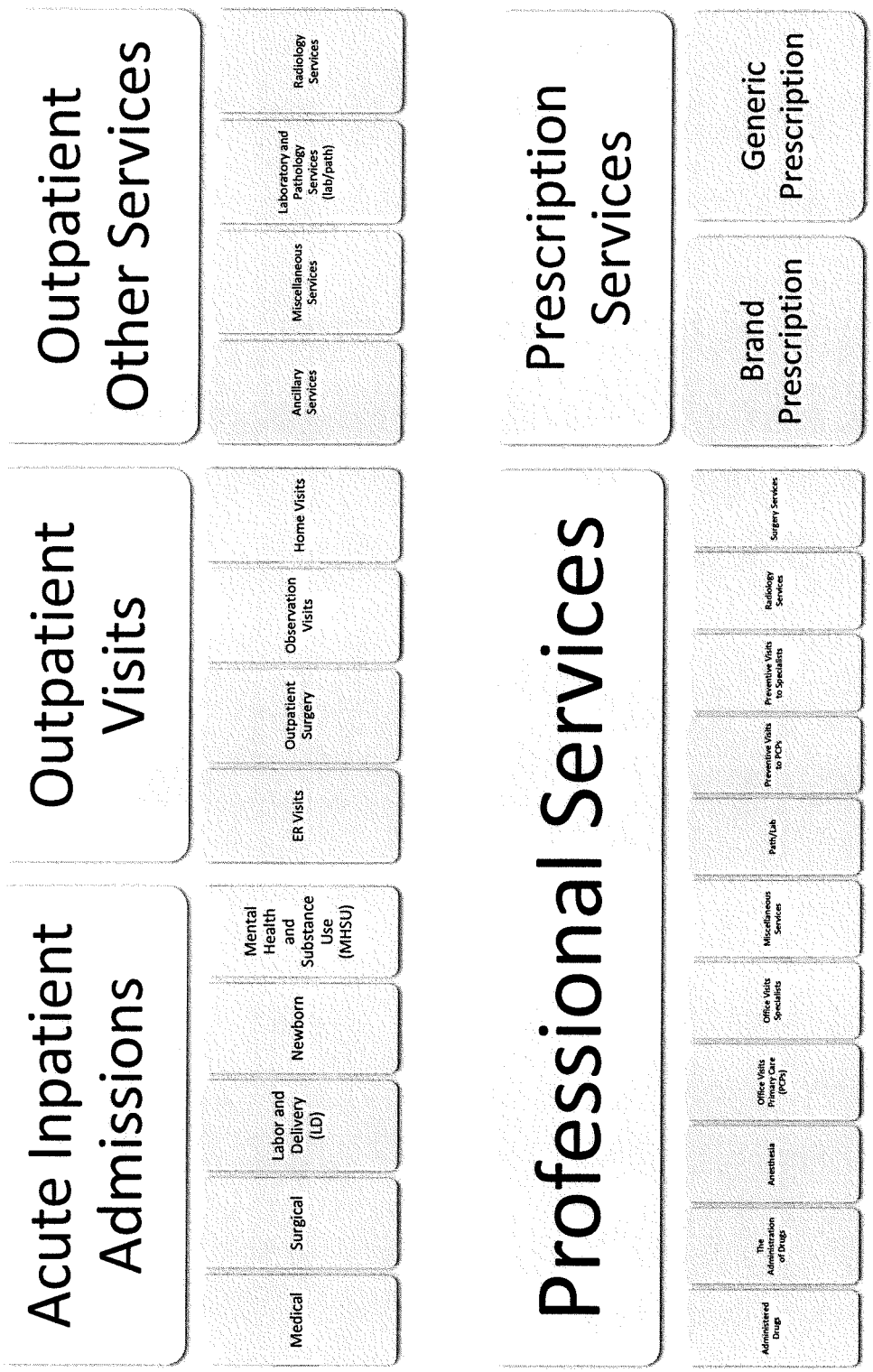
FIG. 8 is a conceptual diagram of subgroup concepts in the HC service hierarchy model.

This component is in charge of interacting with the clinicians who input the seed of resources utilization related terms into the system. According to the clinicians the terms will be grouped in five main groups. These top level concepts of the HC services model are (as shown in FIG. 7):

Acute Inpatient Admissions
Outpatient Visits
Outpatient Other Services
Professional Services
Prescription Services These concepts are to be grouped in the following subgroups (as shown in FIG. 8)

Acute Inpatient Admissions
Medical
Surgical
Labor and Delivery (LD)
Newborn
Mental Health and Substance Use (MHSU)
Outpatient Visits
Emergency Visits (ER Visits)
Outpatient Surgery
Observation Visits
Home Visits
Outpatient Other Services
Auxiliary Services
Miscellaneous Services
Laboratory and Pathology Services (Lab/path)
Radiology Services
Professional Services
Administered Drugs
The Administration of Drugs
Anaesthesia
Office Visits Primary Care (PCPs)
Office Visits Specialists
Miscellaneous Services
Path/Lab
Preventive Visits to PCPs
Preventive Visits to Specialists
Radiology Services
Surgery Services
Prescription Services
Brand Prescription
Generic Prescription It is worth mentioning that this can be a tentative and initial set of terms suggested by the clinicians' expertise, it is not an exhaustive or complete, and can be supplemented as necessary. Moreover, it only includes health care services.

Regarding the classification of the resources terms, they do not necessarily have a hierarchy scheme. Since resources are physical items, people, time, etc. the presentation of the resources' collector will be a list of terms or cluster of terms more than a hierarchy itself.

Taking into account this approach, the categorized list of health care resources terms can be extracted from the healthcare literature and the clinicians' expertise. Categories can be, for example, time taken, people resource, administrative people resource and item resource, as exemplified in the excerpt of seed terms below.

Time resource
Time of visit
Time of surgery
Time of journey to home visits
Time of delay/wait
People resource
Clinicians
Number of doctors
Number of nurses
Administrative/management people
Number of receptionists
Number of consultants
Number of porters
Number of other people involved
Item resource
Beds
Ambulance
Number of prescriptions (related to Drug Prescription in PCO)
Number of operation rooms
Number of post-operation rooms
Number of recovery rooms
Number of waiting rooms
Number of surgical items required
Number of tests
Number of visits/observations
Breakfast/Lunch/Dinner Finally, the component will collect and store the enhanced sets of terms into the system.

Healthcare Entity Reconciliation 90

This component aims at identifying multiple representation of the same real-word object, in other words identifying equivalent terms in the two different data sources. In this particular case this may be by performing matching/alignment between the collected terms from the clinicians and one or more public data sources offering a standardized (and maybe multilingual) vocabulary of terms related to health care services and/or resources. The outcome of the component is to have the enhanced set of terms, proposed by the clinicians, annotated in standardized terms.

Figure 9:
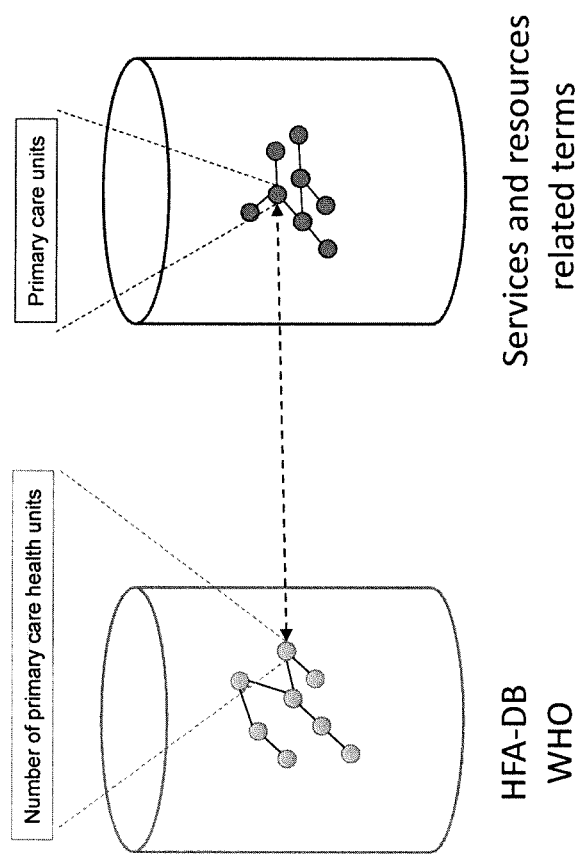
FIG. 9 shows an example of reconciliation between a term in a standard database and a similar term from clinician input.

FIG. 9 shows an overview example of reconciliation between the HFA-DB term "Number of primary care health units" from WHO and the services and resources related term "primary care unit" from clinician input.

Model for Services and Resources Builder 100

Figure 10:
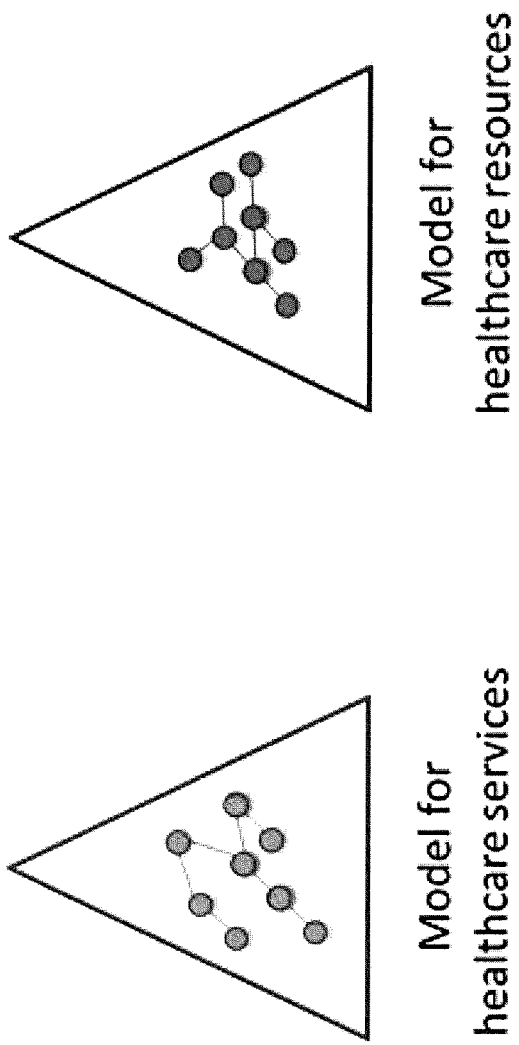
FIG. 10 is an overview of the output of the model builder.
Figure 11:
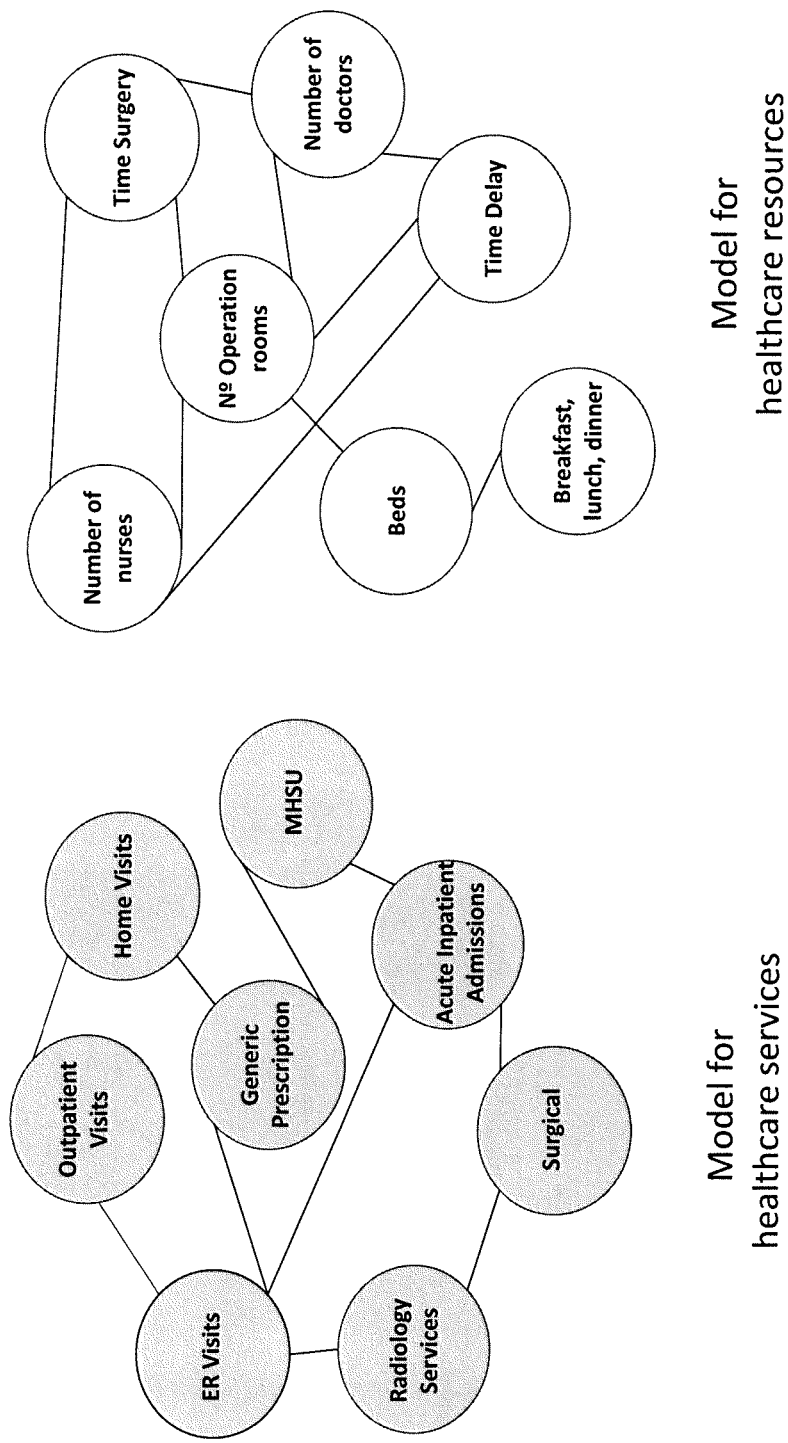
FIG. 11 illustrates exemplary vertices of both models and their internal connections.

This component takes as input the set of terms and their relations and creates an initial set of two models, 110 and 120, one for representing the information of healthcare services and other for representing healthcare resources. FIGS. 10 and 11 present the output of this component.

FIG. 10 is an overview of the output of the model builder, showing the two separate models. FIG. 11 illustrates exemplary vertices of both models and their internal connections, which are formed according to the structure of the clinician information and of the open health data used.

Matcher of Services and Resources Models 130

Once we have the two models representing healthcare services and resources, it is time to create relations between those services and resources. This component is in charge of creating links that relates healthcare services with the resources.

Basically, the component extracts the relations, by performing a relation mining analysis, of the previously identified entities from the public data sources, which are part of the models for healthcare services and resources. The extracted relations will also have a score based on the number of occurrences of the relations within the open data standards/public data sources. For example, the score may be derived from the number of co-occurrences of the terms divided by the sum of the occurrences of either term, or some other suitable metric.

The relations may be labeled with their significance, for example a service may have a particular resource, or a service may imply the presence of a resource and vice versa.

Figure 12:
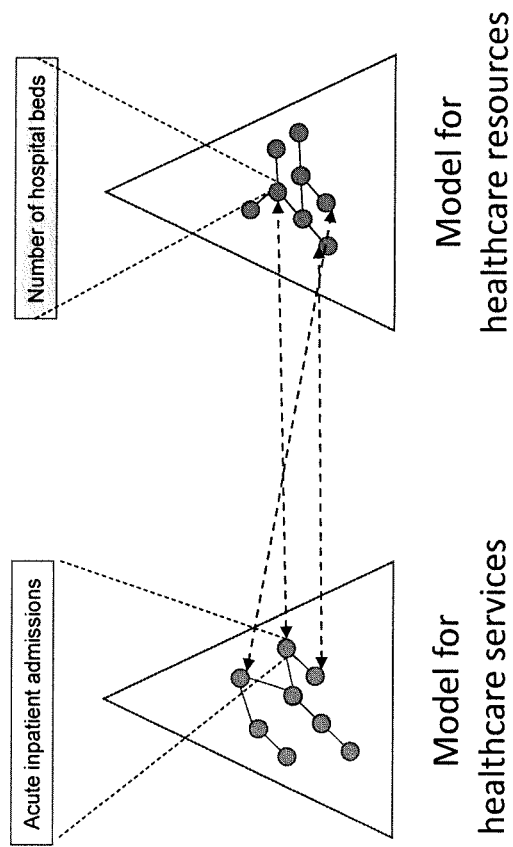
FIG. 12 presents a basic example of the output of the matcher.

FIG. 12 presents a basic example of the output of the matcher, showing a link between acute inpatient admissions and number of hospital beds.

Figure 13:
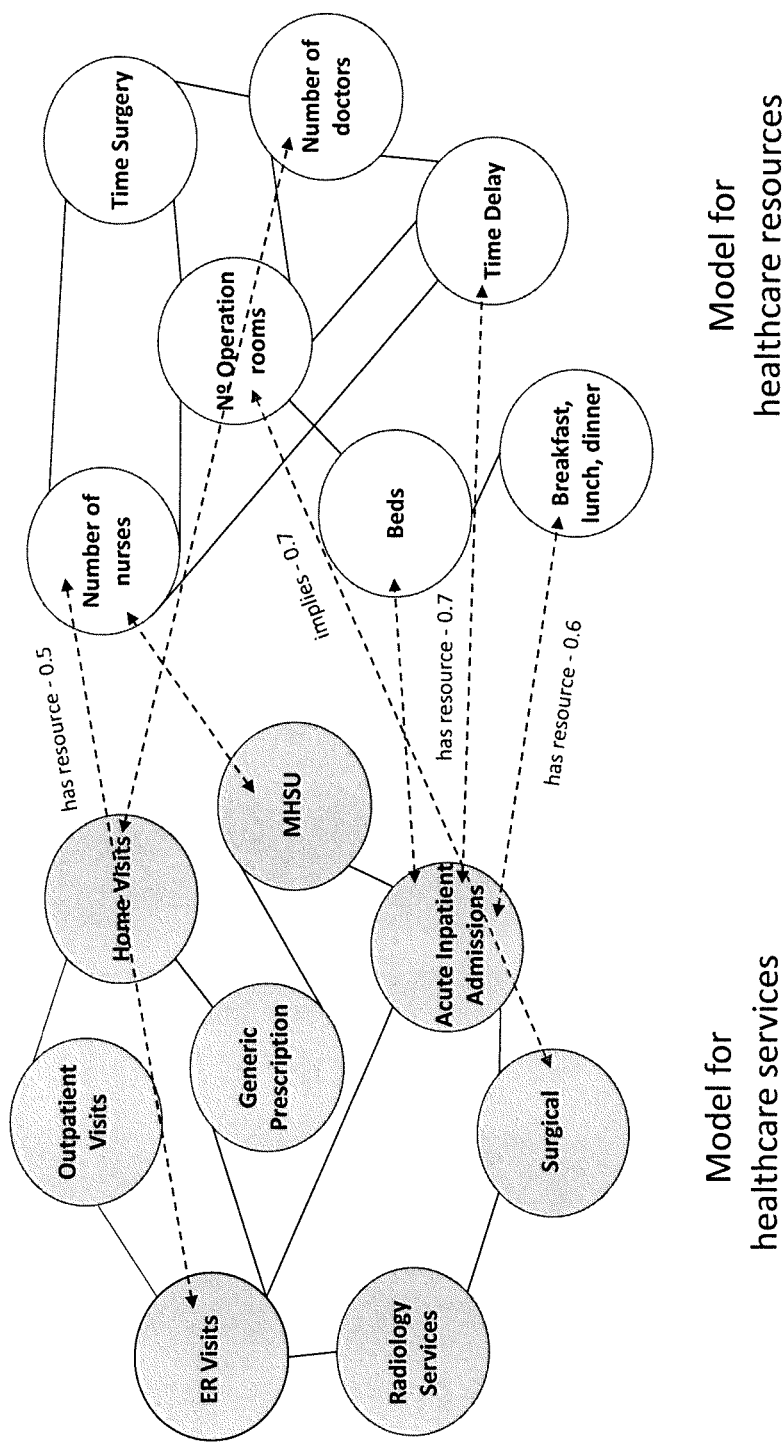
FIG. 13 is a more contextualized example of the output for the matcher.

FIG. 13 is a more contextualized example of the output for the matcher of services and resources models, showing the scores for some exemplary relations.

Knowledge Graph Curator 140

The final module aims at integrating the extracted entities along with their relations, including the scores information mentioned above and the provenance information.

Figure 14:
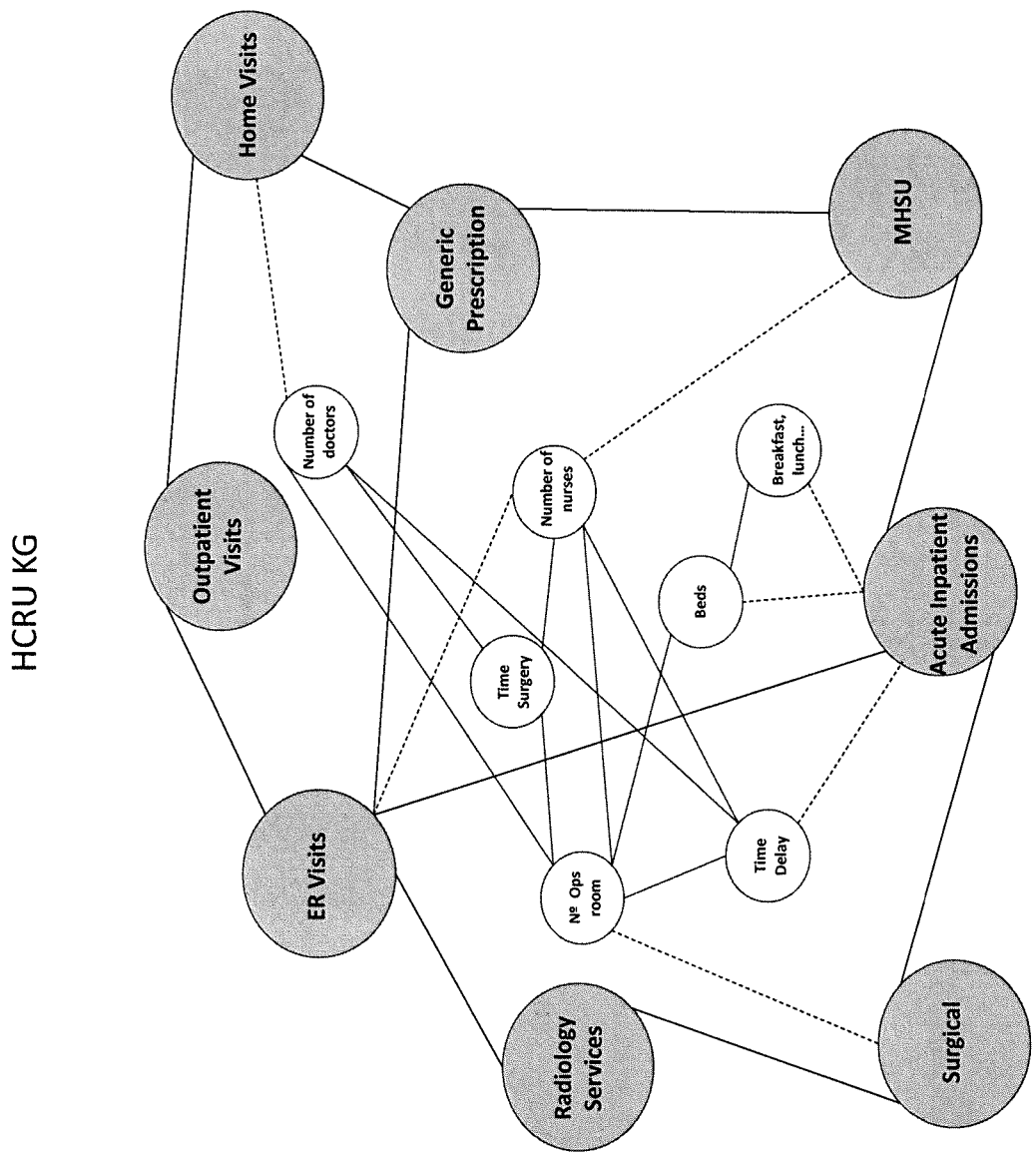
FIG. 14 is a diagram of a knowledge graph in part.

FIG. 14 shows part of an HCRU KG, with the services distinguished from the resources using paler shading.

The system presents the HealthCare Resources Utilization Knowledge Graph to the clinicians in a very intuitive way, (in graph form, as shown in FIG. 14) and they will be able to manually curate and fix any potential inconsistencies of the generated graph.

HCRU KG Customizer 40

Figure 15:
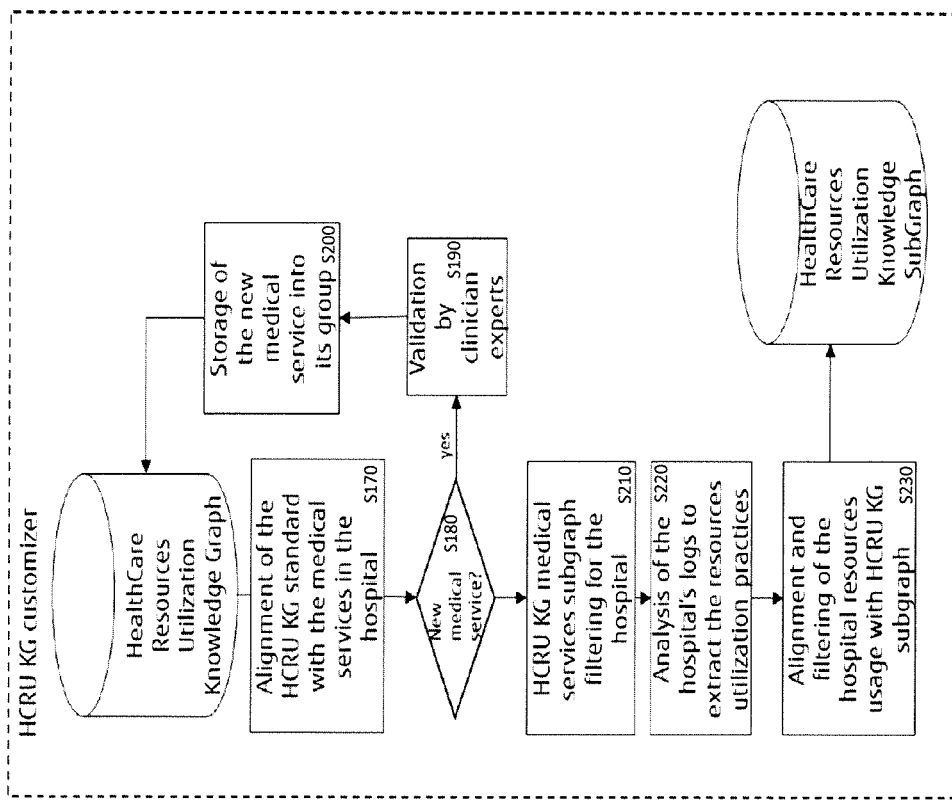
FIG. 15 depicts the main flow of the HCRU KG Customizer 40.

FIG. 15 depicts the main flow of the HCRU KG Customizer 40. This sub-module comprises components which:
- align the standard HCRU Knowledge Graph of medical services with the services that are provided within a particular healthcare institution (S170).
- Check for a new medical service which is not in the HCRU KG (S180), validate the service by clinicians (S190) and store the new medical service in the correct group (S200)
- filter and prune the standard to generate a customized subgraph with the medical services of the institution (S210).
- perform process mining over available hospital logs and extract behaviour patterns of the resources utilization for a particular medical institution (S220).
- filter, generate and customize a subgraph from the previous knowledge subgraph taking into account the resource utilization guidelines of a medical institution (S230).

Figure 16:
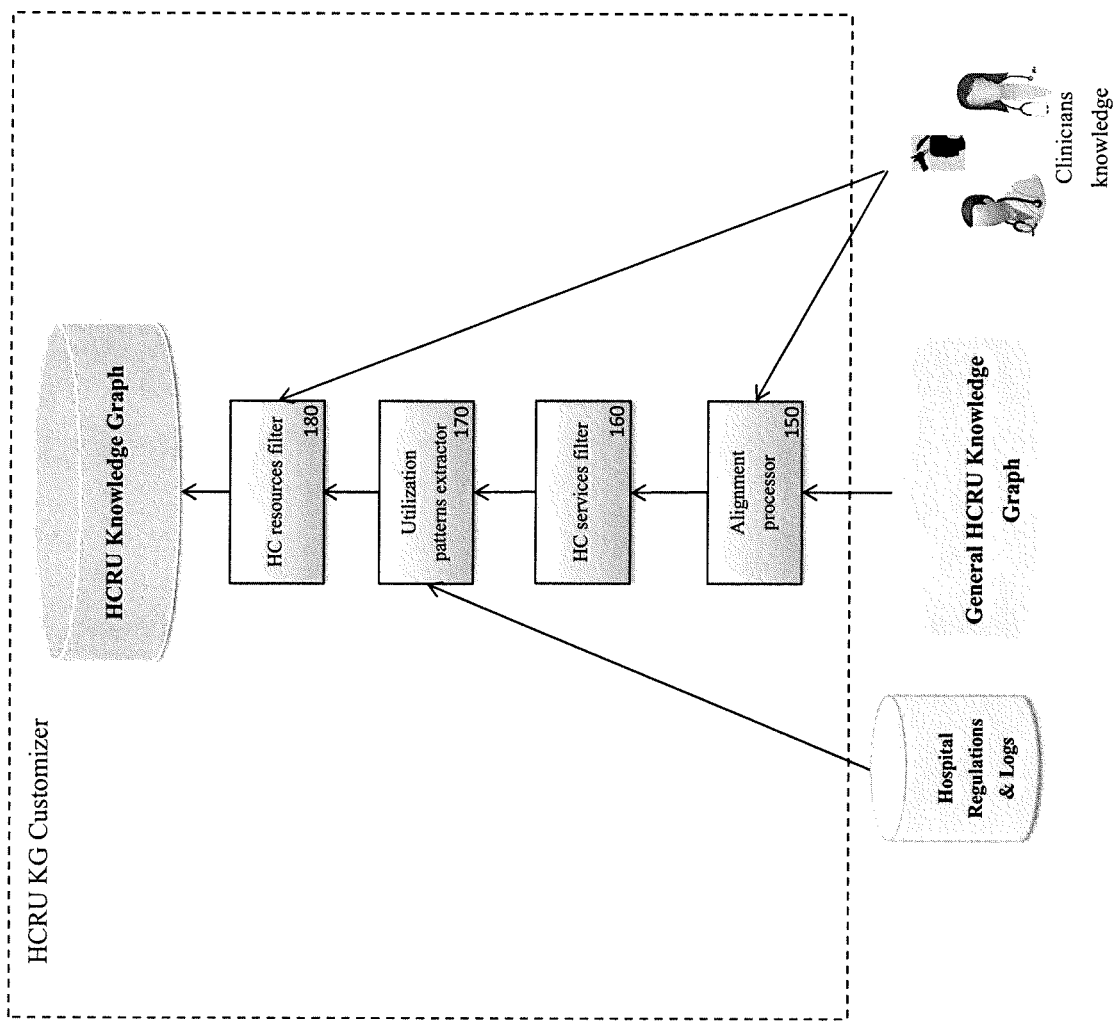
FIG. 16 illustrates the main components of the HCRU KG Customizer.

FIG. 16 illustrates the main components of the HCRU KG Customizer. This sub-module can customize the standard healthcare resources utilization knowledge graph for a particular medical institution. The various components of the customizer are described in the following.

The Alignment processor 150 takes the hospital services portfolio and identifies the services that are contained in the General HCRU KG. Next, the HC services filter 160 removes from the General HCRU KG the services not included in the hospital services portfolio. After that, the Utilization patterns extractor 170, by means of process mining techniques over the Hospital Regulations and Logs, identifies what and how the resources of the hospital are really used. Finally, the HC resources filter 180 removes out all the resources that are not used in the hospital, and it produces the HCRU Knowledge Graph.

One core component of this HCRU KG Customizer is the Utilization patterns extractor 180, which takes the hospital logs, and extracts process knowledge, e.g., process models in order to discover, monitor and improve the healthcare processes specific for the given hospital. A hospital log can be seen as a record of named activities ("Check Medications", "Patient Examination") which is created as a by-product of EHR use. These events occur in an order relative to each other, usually represented by time stamps. In this context, the component checks if the observed behavior in the logs conforms to the given model, provided by the hospital internal regulations. For example, it may be checked whether a medical guideline which states that always a lab test and an X-ray needs to be done is always followed.

Figure 17:
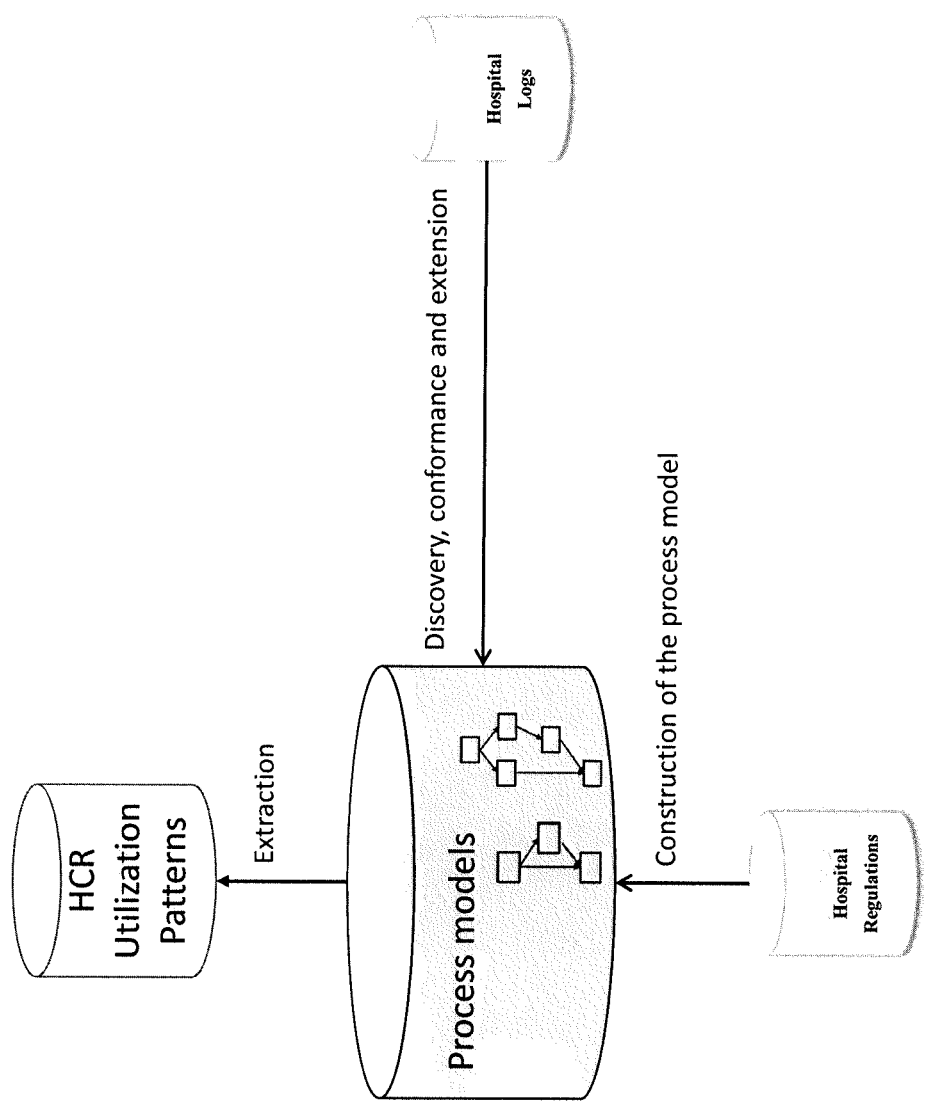
FIG. 17 is a high-level flow diagram of the utilization patterns extractor.

Moreover, the component performs a projection of the information extracted from the logs onto the model, i.e., the hospital internal regulation in this case. For example, performance information may be projected on a discovered healthcare process in order to see for which examinations a long waiting time exists. FIG. 17 shows the flow of this component for this, in which the hospital logs and hospital regulations are matched and patterns extracted to provide HCR utilization patterns.

The HCR utilization pattern contains a customized subgraph of the HCRU KG. This customized subgraph of the HCRU KG will be part of the HCRU KG. As a first approach it is possible to rely on existing, available, and basic approaches for process mining to provide the subgraph.

As previously mentioned, and as seen in FIG. 16, the input of the extractor is the customized version of the HCRU KG for a particular hospital according to the specific services and resources that the given hospital provides. In addition, by checking the logs and internal regulations we can identify how the services and resources are really used by the hospital and modify the subgraph accordingly.

The clinicians and managers will be able to check how the healthcare resources and services are actually used within the hospital. This information will help to enrich the PCO of a particular patient, by including the resources and services the patient is using. In addition this will help with the estimation of the healthcare resource utilization for a potential diagnoses, if the impact estimator module is also used.

Patient HCRU Engine 50

Figure 18:
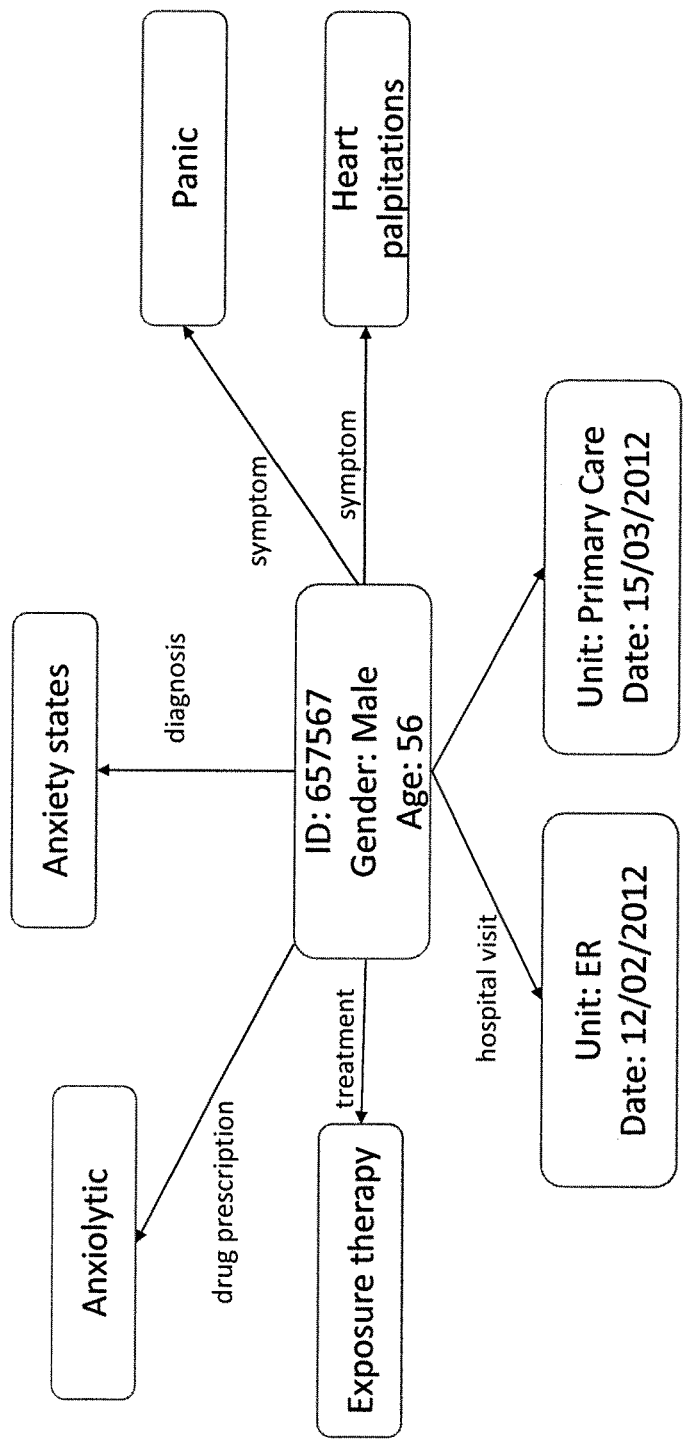
FIG. 18 is an example of a simple PCO.
Figure 19:
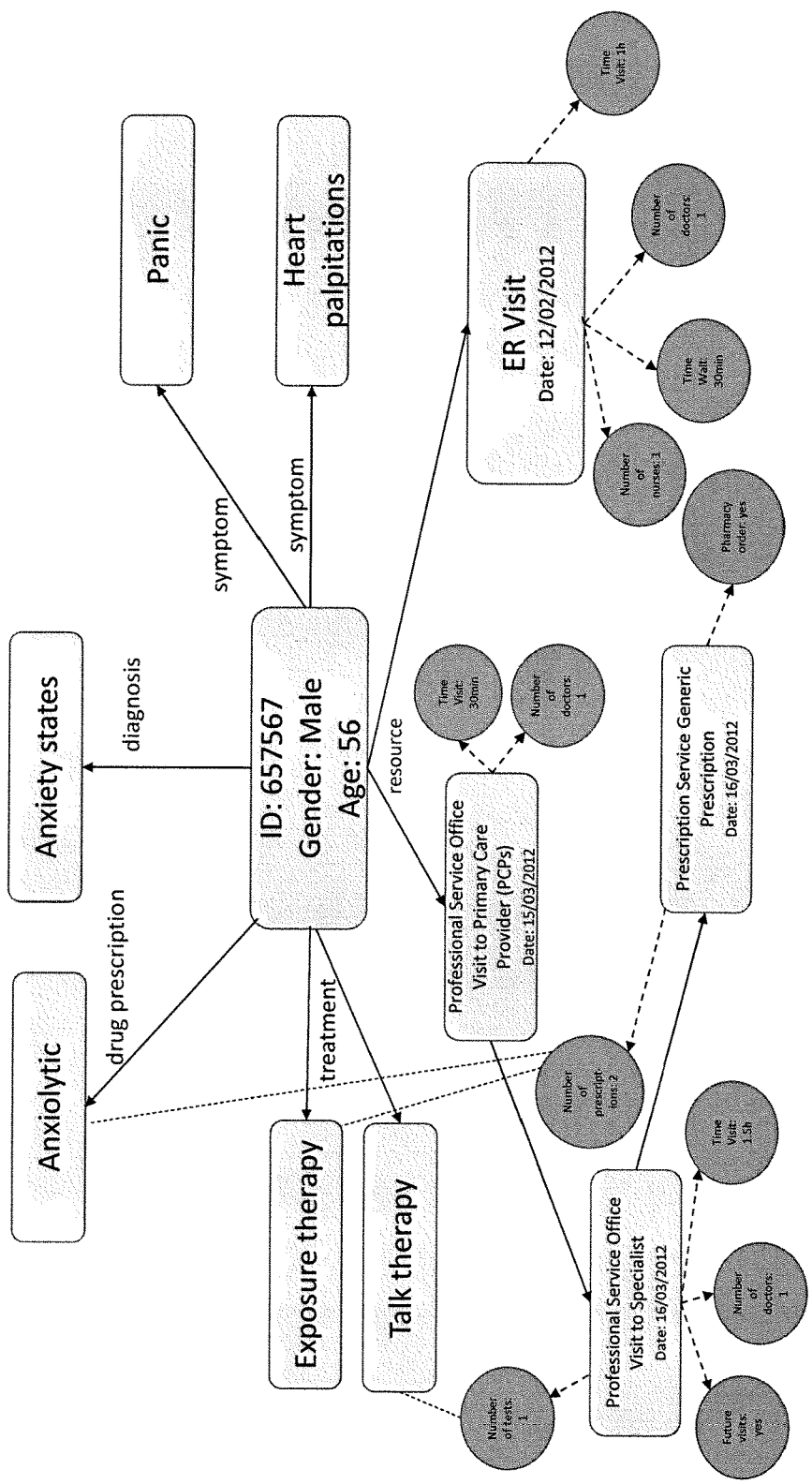
FIG. 19 is an example of a PCO enriched with the HCRU subgraph.

This engine enriches the Patient Clinical Object (PCO) by including information related to the health care resource utilization taken from the HCRU Knowledge Graph. Basically, the module annotates and associates the patient clinical history with concepts from the HCRU. FIG. 18 shows an example of a PCO, and FIG. 19 shows the resultant PCO enriched with the health care resource utilization graph.

The former PCO contains information about clinical history, diagnoses, risks, treatments, symptoms, and drugs. After the enrichment the PCO will include the information about health care resources as exemplified in FIG. 19. In a nutshell, the HCRU KG customized subgraph provides information related to the health care resources, and this information is matched against the clinical history of the PCO, e.g., ER visits or inpatients. Those visits imply that the patient have used some health care resources of the given hospital. Therefore, the enriched (or annotated) PCO reflects this information in FIG. 16.

This enrichment the PCO of a particular patient, by including the resources and services the patient is using will help to identify what resources/services the patient is using and how well or poorly the patient is using the resources/services. Moreover, this will also help to estimate what healthcare resources the patient will use in the future. Finally, the managers will have in a single snapshot what healthcare resources are being used by the patients.

Impact Estimator 60

This module takes as input the annotated PCO that already includes the health care resource utilization (as a subgraph) for the particular patient; the potential new diagnosis for such patient; and the HCRCU Knowledge Graph. The module produces as result a subgraph of the potential health care resource utilization along with their scores. Nodes of this resultant subgraph, which correspond to the health care resources, have a score that represents the probability of potential use (for that health care resource) for the particular patient when the potential diagnosis is given.

Figure 20:
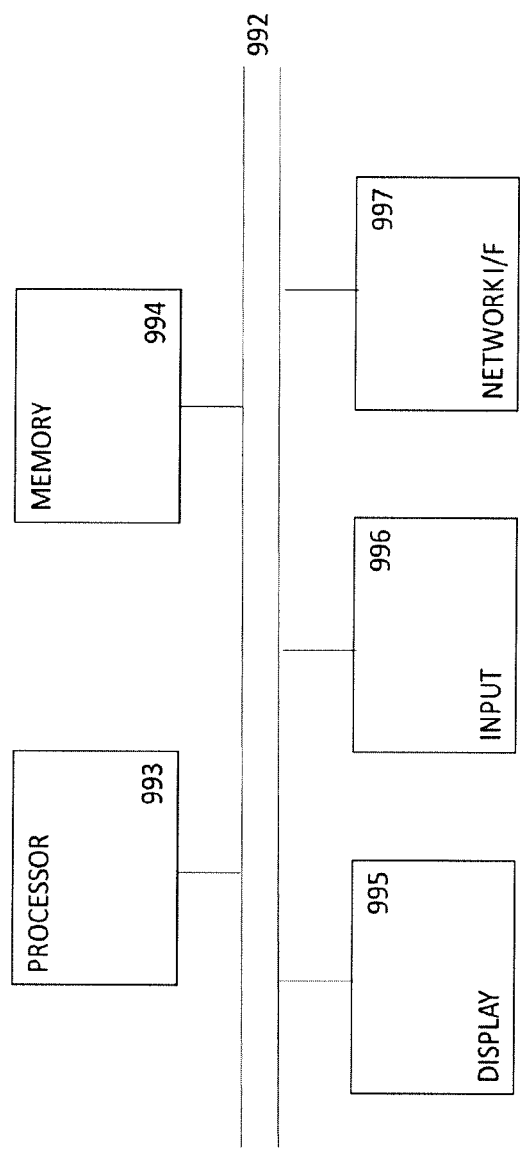
FIG. 20 is a diagram of hardware which is suitable to implement the embodiments.

FIG. 20 is a block diagram of a computing device, such as a data storage server, and which may be used to implement a method of an embodiment of a computer-implemented method to identify healthcare resources used by a patient of a medical institution. The computing device comprises a processor 993, and memory, 994. Optionally, the computing device also includes a network interface 997 for communication with other computing devices, for example with other computing devices of the embodiments.

For example, an embodiment may be composed of a network of such computing devices. Optionally, the computing device also includes one or more input mechanisms such as keyboard and mouse 996, and a display unit such as one or more monitors 995. The components are connectable to one another via a bus 992.

The memory 994 may include a computer readable medium, which term may refer to a single medium or multiple media (e.g., a centralized or distributed database and/or associated caches and servers) configured to carry computer-executable instructions or have data structures stored thereon. Computer-executable instructions may include, for example, instructions and data accessible by and causing a general purpose computer, special purpose computer, or special purpose processing device (e.g., one or more processors) to perform one or more functions or operations. Thus, the term "computer-readable storage medium" may also include any medium that is capable of storing, encoding or carrying a set of instructions for execution by the machine and that cause the machine to perform any one or more of the methods of the present disclosure. The term "computer-readable storage medium" may accordingly be taken to include, but not be limited to, solid-state memories, optical media and magnetic media. By way of example, and not limitation, such computer-readable media may include non-transitory computer-readable storage media, including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices).

The processor 993 is configured to control the computing device and execute processing operations, for example executing code stored in the memory to implement the various different functions of modules described here and in the claims. The memory 994 stores data being read and written by the processor 993. As referred to herein, a processor may include one or more general-purpose processing devices such as a microprocessor, central processing unit, or the like. The processor may include a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also include one or more special-purpose processing devices such as an application specific integrated circuit (ASIC), a field programmable gate array (FPGA), a digital signal processor (DSP), network processor, or the like. In one or more embodiments, a processor is configured to execute instructions for performing the operations and steps discussed herein.

The display unit 997 may display a representation of data stored by the computing device, such as the HCRU KG, or part thereof, or the PCO or part thereof and may also display a cursor and dialog boxes and screens enabling interaction between a user and the programs and data stored on the computing device. The input mechanisms 996 may enable a user to input data and instructions to the computing device. For example it can allow a clinician to enter or amend the seed terms used for medical services and healthcare resources.

The network interface (network I/F) 997 may be connected to a network, such as the Internet, and is connectable to other such computing devices via the network, for example to access open data. The network I/F 997 may control data input/output from/to other apparatus via the network. Other peripheral devices such as microphone, speakers, printer, power supply unit, fan, case, scanner, trackerball etc may be included in the computing device.

The knowledge graph (or HCRU KG) builder may comprise processing instructions stored on a portion of the memory 994, the processor 993 to execute the processing instructions, and a portion of the memory 994 to store the data making up the HCRU KG during the execution of the processing instructions. The HCRU KG may be stored on the memory 994 and/or on a connected storage unit.

The knowledge graph (or HCRU KG) customizer may comprise processing instructions stored on a portion of the memory 994, the processor 993 to execute the processing instructions, and a portion of the memory 994 to store data contributing to the customized subgraph during the execution of the processing instructions. The customized subgraph may be stored on the memory 994 and/or on a connected storage unit.

The patient HCRU engine may comprise processing instructions stored on a portion of the memory 994, the processor 993 to execute the processing instructions, and a portion of the memory 994 to store data making up the enriched PCO during the execution of the processing instructions. The enriched PCO may be stored on the memory 994 and/or on a connected storage unit.

Methods of the present embodiments may be carried out on a computing device such as that illustrated in FIG. 20. Such a computing device need not have every component illustrated in FIG. 20, and may be composed of a subset of those components. A method of the present the embodiments may be carried out by a single computing device in communication with one or more data storage servers via a network. The computing device may be a data storage itself storing the resultant graphs in of the embodiments.

A method of the embodiments may be carried out by a plurality of computing devices operating in cooperation with one another. One or more of the plurality of computing devices may be a data storage server storing at least a portion of the graphs.

Key Benefits

Some key benefits lie in providing a mechanism that allows creation of a healthcare resource utilization knowledge graph, with the support of the clinicians, which is the foundation to identify patient resources utilization in a more accurate way.

In a nutshell, providing the associated health care resource utilization of a particular patient helps to find the best sources of support, as well making decisions about the future. For example, particular embodiments can:

Identify group of patients that are using similar healthcare resources, and in this way what health care resources are mostly used in a particular hospital.

Once we have a new patient we can classify him/her in one these groups and estimate what resources he/she will be using.

The hospital will know what healthcare resources need more attention given the patients the hospital has.

Moreover, some solutions are able to detect the potential impact of particular diagnosis for the patients, estimating in this way the resources he/she is going to use. This could be expanded to a whole group of patients, for overall scheduling of resources in a hospital information system.

Brief Description of Technical Terms Used

Health Care Utilization: The measure of the population's use of the health care services available to them. This includes the utilization of Hospital resources, Personal Care Home (PCH) resources, and physician resources. Health care utilization and health status are used to examine how efficiently a health care system produces health in a population.

Health status: An indication of the risk of death of patients based on the type and number of co-morbid conditions or on a number of socio-economic indicators.

Medical treatment: the management and care of a patient, it includes nursing, psychological intervention and specialist mental health rehabilitation.

Diagnosis: the process of determining by examination the nature and circumstance of a disease condition from its signs and symptoms Drugs: something that treats or prevents or alleviates the symptoms of a disease.

Health care services means the furnishing of medicine, medical or surgical treatment, nursing, hospital service, dental service, optometrical service, complementary health services or any or all of the enumerated services or any other necessary services of like character, whether or not contingent upon sickness or personal injury, as well as the furnishing to any person of any and all other services and goods for the purpose of preventing, alleviating, curing or healing human illness, physical disability or injury.

Health resources are all materials, personnel, facilities, funds, and anything else that can be used for providing health care and services.

Although a few embodiments have been shown and described, it would be appreciated by those skilled in the art that changes may be made in these embodiments without departing from the principles and spirit of the embodiments, the scope of which is defined in the claims and their equivalents.

What is claimed is:

1. A computer apparatus to identify healthcare resources used by a medical institution, comprising:
a memory storing instructions that when executed provide a knowledge graph builder, a knowledge graph customizer, a patient healthcare resource utilization (HCRU) engine and an impact estimator; and
a processor configured to,
via the knowledge graph builder,
input, via an interface, open data, clinician information, a patient clinical object (PCO) which represents the patient as a patient graph, and at least one of an electronic medical institution log and a set of internal regulations of the medical institution,
generate a set of medical services terms based on a division of medical services into at least one of admissions, outpatient services, professional services and prescription services and a set of medical resources terms based on at least one of people, items and time taken derived from the open data and the clinician information, and
associate medical resources with medical services to build a knowledge graph, and
provide scores within the knowledge graph, the scores representing the number of co-occurrences of either medical service terms or medical resources terms; and
via the knowledge graph customizer,
match the knowledge graph with at least one of the electronic medical institution log and the internal regulations of the medical institution to provide a customized subgraph of the knowledge graph which is specific to the medical institution, by operations that
identify provided services of the medical institution represented in the knowledge graph,
filter out unprovided services in the knowledge graph that are not provided by the medical institution,
discover, by process mining, how the medical resources are used in the medical institution,
identify, from medical institution data, available resources used in the medical institution, and
remove unavailable resources from the knowledge graph that are not available in the medical institution;
via the patient HCRU engine, use the customized subgraph to associate and annotate the PCO with relevant healthcare resource utilization information by identifying healthcare resources of the medical institution used by the patient; and
via the impact estimator, use the scores in connection with the annotated PCO and a potential diagnosis for the patient to determine a probability of potential use of a particular health care resource for the patient when the potential diagnosis is given.

2. A computer apparatus according to claim 1, wherein the processor is further configured, via the knowledge graph builder, to
collect seeds for an initial set of medical services terms and for an initial set of medical resources terms from the clinician information, and
reconcile collected initial sets of terms from clinicians with the open data to provide an enhanced set of terms proposed by the clinicians and annotated using the open data.

3. A computer apparatus according to claim 1, wherein the processor is further configured, via the knowledge graph builder, to create two models, one representing healthcare resources and another representing healthcare services.

4. A computer apparatus according to claim 1,
wherein both the electronic medical institution log and the set of internal regulations of the medical institution are input, and
wherein the processor is further configured, via the knowledge graph customizer, to
extract process knowledge from the electronic medical institution log, and
project extracted process knowledge onto the internal regulations of the medical institution to check if the extracted process knowledge conforms to the internal regulations of the medical institution.

5. A computer apparatus according to claim 1, wherein the processor is further configured, via the patient HCRU engine, to
access clinical data present in the PCO, and
add links to new vertices representing healthcare resources by reference to the customized subgraph of the knowledge graph as a template.

6. A computer apparatus according to claim 1,
wherein the PCO is provided as a vertex graph centered on a patient ID vertex, with edges linking the patient ID vertex to vertices representing clinical data, and
wherein the processor is further configured, via the patient HCRU engine, to match clinical vertices representing the clinical data to knowledge vertices of the knowledge graph.

7. A computer apparatus according to claim 1, wherein: the PCO is limited to one or more of: a condition, an episode of a condition, a timeframe, and a diagnosis.

8. A computer apparatus according to claim 1, wherein the processor is further configured to
identify healthcare resources used by a population of patients of the medical institution, based on a patient clinical object (PCO) for each patient, and
by reference to the customized subgraph, associate and annotate each PCO with relevant healthcare resource utilization information.

9. A computer-implemented method to identify healthcare resources used by a medical institution, comprising:
inputting open data and clinician information;
generating a set of medical services terms based on a division of medical services into at least one of admissions, outpatient services, professional services and prescription services and a set of medical resources terms based on at least one of people, items and time taken from the open data and clinician information;
associating medical resources with medical services to build a knowledge graph;
providing, within the knowledge graph, scores representing a number of co-occurrences of either medical service terms or medical resources terms;
inputting at least one of an electronic medical institution log and a set of internal regulations of the medical institution;
matching the knowledge graph with the at least one of the electronic medical institution log and the set of internal regulations of the medical institution to provide a customized subgraph of the knowledge graph which is specific to the medical institution, thereby customizing the knowledge graph by
identifying provided services of the medical institution represented in the knowledge graph,
filtering out unprovided services in the knowledge graph that are not provided by the medical institution,
discovering, by process mining, how resources are used in the medical institution,
identifying, from medical institution data, available resources used in the medical institution, and
removing unavailable resources from the knowledge graph that are not available in the medical institution;
inputting a patient clinical object (PCO) which represents a patient as a patient graph;
using the customized subgraph to associate and annotate the PCO with relevant healthcare resource utilization information by identifying healthcare resources of the medical institution used by the patient; and
using the scores in connection with the annotated PCO and a potential diagnosis for the patient to determine a probability of potential use of a particular health care resource for the patient when the potential diagnosis is given.

10. A non-transitory computer-readable medium storing a computer program which when executed on a computer carries out a method to identify healthcare resources used by a medical institution, the method comprising:
inputting open data and clinician information;
generating a set of medical services terms based on a division of medical services into at least one of admissions, outpatient services, professional services and prescription services and a set of medical resources terms based on at least one of people, items and time taken from the open data and clinician information;
associating medical resources with medical services to build a knowledge graph;
providing, within the knowledge graph, scores representing a number of co-occurrences of either medical service terms or medical resources terms;
inputting at least one of an electronic medical institution log and a set of internal regulations of the medical institution;
matching the knowledge graph with the at least one of the electronic medical institution log and the set of internal regulations of the medical institution to provide a customized subgraph of the knowledge graph which is specific to the medical institution, thereby customizing the knowledge graph by
identifying provided services of the medical institution represented in the knowledge graph,
filtering out unprovided services in the knowledge graph that are not provided by the medical institution,
discovering by process mining how resources are used in the medical institution, identifying, from medical institution data, available resources are used in the medical institution, and
removing unavailable resources from the knowledge graph that are not available in the medical institution;
inputting a patient clinical object (PCO) which represents a patient as a patient graph;
using the customized subgraph to associate and annotate the PCO with relevant healthcare resource utilization information by identifying healthcare resources of the medical institution used by the patient; and
using the scores in connection with the annotated PCO and a potential diagnosis for the patient to determine a probability of potential use of a particular health care resource for the patient when the potential diagnosis is given.

* * * * *